US009175308B2

(12) United States Patent
Shiku et al.

(10) Patent No.: US 9,175,308 B2
(45) Date of Patent: Nov. 3, 2015

(54) CHIMERIC ANTIGEN RECEPTOR

(71) Applicants: MIE UNIVERSITY, Mie (JP); TAKARA BIO INC., Shiga (JP)

(72) Inventors: Hiroshi Shiku, Mie (JP); Yuki Orito, Mie (JP); Junichi Mineno, Shiga (JP); Sachiko Okamoto, Shiga (JP); Yasunori Amaishi, Shiga (JP)

(73) Assignees: MIE UNIVERSITY, Mie (JP); TAKARA BIO INC., Shiga (JP)

( * ) Notice: Subject to any disclaimer, the term of this patent is extended or adjusted under 35 U.S.C. 154(b) by 0 days.

(21) Appl. No.: 14/349,763

(22) PCT Filed: Oct. 5, 2012

(86) PCT No.: PCT/JP2012/076034
§ 371 (c)(1),
(2) Date: Apr. 4, 2014

(87) PCT Pub. No.: WO2013/051718
PCT Pub. Date: Apr. 11, 2013

(65) Prior Publication Data
US 2014/0242701 A1    Aug. 28, 2014

(30) Foreign Application Priority Data
Oct. 7, 2011    (JP) .................................. 2011-222510

(51) Int. Cl.
| C12N 5/10 | (2006.01) |
| C12N 5/0783 | (2010.01) |
| C07H 21/04 | (2006.01) |
| C07K 14/705 | (2006.01) |
| C07K 19/00 | (2006.01) |
| C12N 15/85 | (2006.01) |
| C07K 14/725 | (2006.01) |
| C07K 16/30 | (2006.01) |

(52) U.S. Cl.
CPC ............ *C12N 15/85* (2013.01); *C07K 14/7051* (2013.01); *C07K 14/70517* (2013.01); *C07K 14/70521* (2013.01); *C07K 14/70578* (2013.01); *C07K 14/70596* (2013.01); *C07K 16/30* (2013.01); *C07K 2319/00* (2013.01); *C07K 2319/03* (2013.01); *C07K 2319/30* (2013.01)

(58) Field of Classification Search
CPC ............... C07K 16/28; C07K 2319/00; C07K 2317/622; C07K 2319/33; A61K 35/17; A61K 2039/5156; C12N 5/0636; C12N 2510/00
USPC ............. 536/23.4; 530/387.3; 435/328, 372.3
See application file for complete search history.

(56) References Cited

U.S. PATENT DOCUMENTS

| 6,103,521 A * | 8/2000 | Capon et al. .................. 435/325 |
| 2002/0098525 A1 | 7/2002 | Ni et al. |
| 2006/0025576 A1 | 2/2006 | Miller et al. |

FOREIGN PATENT DOCUMENTS

WO    2010/085660    7/2010

OTHER PUBLICATIONS

Sadelain et al. (2009) Current Opinion in Immunology, vol. 21(2), 215-233.*
Ronchetti et al. (2007) J. Immunol., vol. 179, 5916-5926.*
International Search Report dated Nov. 20, 2012 issued in corresponding International (PCT) Application No. PCT/JP2012/076034.
Notification of Transmittal of Translation of the International Preliminary Report on Patentability dated Apr. 17, 2014 in corresponding International (PCT) Application No. PCT/JP2012/076034.
Sadelain, M., et al., "The Promise and Potential Pitfalls of Chimeric Antigen Receptors", Current Opinion in Immunology, 2009, vol. 21, No. 2, p. 215-223.
Tsukahara, T., "Adoptive Immuno-Gene Therapy for Refractory B-cell Malignancy With Chimeric Antigen Receptor-Expressing T-cells", Journal of Clinical and Experimental Medicine, 2011, vol. 237, No. 3, p. 223-226, with English language abstract.
Kohm, A. P., et al. "CD28 Regulates Glucocorticoid-Induced TNF Receptor Family-Related Gene Expression on CD4+ T Cells via IL-2-Dependent Mechanisms", Cellular Immunology, 2005, vol. 235, No. 1, p. 56-64.
Esparza, E. M., et al., "Glucocorticoid-Induced TNF Receptor Functions as a Costimulatory Receptor That Promotes Survival in Early Phases of T Cell Activation" The Journal of Immunology, 2005, vol. 174, No. 12, p. 7869-7874.
Kanamaru, F., et al., "Costimulation via Glucocorticoid-Induced TNF Receptor in Both Conventional and CD25+ Regulatory CD4+ T Cells", The Journal of Immunology, 2004, vol. 172, No. 12, p. 7306-7314.
McHugh, R. S., et al., "CD4+ CD25+ Immunoregulatory T Cells: Gene Expression Analysis Reveals a Functional Role for the Glucocorticoid-Induced TNF Receptor", Immunity, 2002, vol. 16, p. 331-323.
Sakaguchi, S., et al., "Immunologic Tolerance Maintained by CD25+ CD4+ Regulatory T Cells: Their Common Role in Controlling Autoimmunity, Tumor Immunity, and Transplantation Tolerance", Immunological Reviews, 2001, vol. 182, p. 18-32.

(Continued)

*Primary Examiner* — Anne Marie S Wehbe
(74) *Attorney, Agent, or Firm* — Wenderoth, Lind & Ponack, L.L.P.

(57) ABSTRACT

Provided are a chimeric antigen receptor comprising an extracellular domain capable of binding to an antigen, a transmembrane domain and at least one intracellular domain, the chimeric antigen receptor being characterized in that an intracellular domain of a glucocorticoid-induced tumor necrosis factor receptor (GITR) is contained as the intracellular domain; a nucleic acid encoding the chimeric antigen receptor; a cell expressing the chimeric antigen receptor; and a method for producing the cell.

8 Claims, 13 Drawing Sheets

(56) References Cited

OTHER PUBLICATIONS

Finney H. M., et al., "Activation of Resting Human Primary T Cells with Chimeric Receptors: Costimulation from CD28, Inducible Costimulator, CD134, and CD137 in Series with Signals from the TCRζ Chain", The Journal of Immunology, 2004, vol. 172, p. 104-113.

Chinese Office Action with Search Report dated May 12, 2015, issued in corresponding Chinese Patent Application No. 201280060330.9 (with English Translation).

Extended European Search Report dated May 18, 2015, issued in corresponding European Patent Application No. 12838701.6.

* cited by examiner

Fig.2

| scFv | Spacer domain | CD28 TM | CD3ζ | | | (1) z |

| scFv | Spacer domain | CD28 TM | CD28 ICD | CD3ζ | | (2) 28z |

| scFv | Spacer domain | CD28 TM | CD3ζ | CD28 ICD | | (3) z28 |

| scFv | Spacer domain | CD28 TM | GITR ICD | CD3ζ | | (4) Gz |

| scFv | Spacer domain | CD28 TM | CD3ζ | GITR ICD | | (5) zG |

| scFv | Spacer domain | CD28 TM | CD28 ICD | GITR ICD | CD3ζ | (6) 28Gz |

| scFv | Spacer domain | GITR TM | GITR ICD | CD28 ICD | CD3ζ | (7) G28z |

| scFv | Spacer domain | CD28 TM | CD3ζ | GITR ICD | CD28 ICD | (8) zG28 |

| scFv | Spacer domain | CD28 TM | CD28 ICD | CD3ζ | GITR ICD | (9) 28zG |

| scFv | Spacer domain | CD28 TM | CD3ζ | CD28 ICD | GITR ICD | (10) z28G |

CHIMERIC ANTIGEN RECEPTOR

TECHNICAL FIELD

The present invention relates to a nucleic acid encoding a chimeric antigen receptor and a cell expressing a chimeric antigen receptor, which are useful in the field of adoptive immunity gene therapy for tumors.

BACKGROUND ART

As a therapeutic strategy for tumors, it can be expected that a gene of a T cell receptor (TCR) capable of binding to a specific antigen is introduced into any T cell to prepare a T cell targeting the antigen of interest. Based on this strategy, adoptive immunity gene therapies using TCR genes targeting many tumor antigens, for example, WT1, MART1, gp100, CEA, CD19 and mHAG HA-2 antigens have been attempted.

As a novel adoptive immunity gene therapy for tumors, attention has been paid to a gene-modified T cell therapy. The gene-modified T cell therapy comprises introducing a nucleic acid encoding a chimeric antigen receptor (CAR) into a T cell, wherein the CAR has specificity for a surface antigen of a tumor cell and ability to activate a T cell, growing ex vivo the gene-introduced T cell thus obtained, and then transfusing the cell into a patient. This therapy is believed to have a stronger and longer-lasted anti-tumor effect than that of an antibody drug, and therefore the clinical effect thereof is greatly expected.

A representative structure of CAR comprises a single chain variable fragment (scFv) recognizing a surface antigen of a tumor cell, a transmembrane domain, and an intracellular domain of a TCR complex CD3ζ that activates a T cell. A CAR having such a constitution is called a first generation CAR. A gene of a single chain variable fragment portion is isolated from, for example, a hybridoma producing a monoclonal antibody that recognizes a target antigen. A T cell expressing a CAR directly recognizes a surface antigen of a tumor cell independently of the expression of major histocompatibility antigen class I on the tumor cell, and at the same time, activates the T cell, and thereby the CAR-expressing T cell can efficiently kill the tumor cell.

For the purpose of enhancing the ability of a first generation CAR to activate a T cell, a second generation CAR has been developed, wherein an intracellular domain of CD28 which is a costimulatory molecule of a T cell is linked to a first generation CAR. As a further improved version, a third generation CAR has also been developed, wherein an intracellular domain derived from CD137 (4-1BB) or CD134 (OX40) which is a tumor necrosis factor (TNF) receptor superfamily is tandemly linked to a first generation CAR. Thus, many CAR molecules targeting variety of tumor antigens have been reported (Non-Patent Document 1). However, costimulatory molecules used as the intracellular domain for the second generation and third generation CARs which are currently reported are limited. It is known that when linked to a CAR, an intracellular domain derived from every costimulatory molecule of a T cell does not uniformly stimulate a T cell strongly to damage a target tumor cell. For example, it has been reported that a second generation CAR in which an intracellular domain derived from CD137 is linked exhibits a cytotoxic activity only to the same extent as that of a first generation CAR, that is, the intracellular domain has no effect in improving the function of a CAR (Non-Patent Document 2). Therefore, finding of a novel costimulatory molecule that is effective when linked to a CAR has been demanded.

A glucocorticoid-induced tumor necrosis factor receptor (GITR) found as a gene being expressed on a regulatory T cell which is a subset of T cells is a transmembrane protein receptor on a cell surface, and is one member of a TNF receptor superfamily (Non-Patent Document 3). A GITR is shown to exist constitutively on a non-activated T cell. A GITR binds to another transmembrane protein called a GITR ligand (hereinafter, referred to as a GITRL). An agonistic antibody to a GITR is shown to eliminate an immunosuppressive activity of a regulatory T cell, which suggests that a GITRL plays a functional role of controlling the activity of a regulatory T cell via a GITR (see Non-Patent Document 4).

CITATION LIST

Non-Patent Document

Non-Patent Document 1: Current Opinion in Immunology, vol. 21, pp. 215-223 (2009)
Non-Patent Document 2: J. Immunology, vol. 172, pp. 104-113 (2004)
Non-Patent Document 3: Immunol. Rev., vol. 182, pp. 18-32 (2001)
Non-Patent Document 4: Immunity, vol. 16, pp. 311-323 (2002)

SUMMARY OF INVENTION

Problems to be Solved by Invention

An object of the present invention is to provide a nucleic acid encoding a CAR which specifically binds to a target antigen and imparts a high cytotoxic activity against a target cell to a cell, and a cell expressing the CAR.

Solution to Problem

The present inventors intensively made efforts in order to solve the aforementioned problems and, as a result, found that a cell expressing a CAR having an intracellular domain of a GITR specifically bound to a target antigen, and had a high cytotoxic activity against a target cell. Thus, the present invention was completed.

The present invention generally relates to the following aspects.

[1] A nucleic acid encoding a chimeric antigen receptor comprising an extracellular domain capable of binding to an antigen, a transmembrane domain, and at least one intracellular domain, wherein the intracellular domain includes an intracellular domain of a glucocorticoid-induced tumor necrosis factor receptor (GITR).

[2] The nucleic acid encoding a chimeric antigen receptor according to [1], wherein the antigen is a tumor antigen.

[3] The nucleic acid encoding a chimeric antigen receptor according to [1], wherein the extracellular domain capable of binding to an antigen is a single chain variable fragment of an antibody that binds to the antigen.

[4] The nucleic acid encoding a chimeric antigen receptor according to [1], wherein the intracellular domain further includes a CD3ζ intracellular domain.

[5] The nucleic acid encoding a chimeric antigen receptor according to [4], wherein the intracellular domain of GITR is arranged on a C-terminal side relative to the CD3ζ intracellular domain.

[6] A chimeric antigen receptor comprising an extracellular domain capable of binding to an antigen, a transmembrane domain, and at least one intracellular domain, wherein the intracellular domain includes an intracellular domain of a GITR.

[7] The chimeric antigen receptor according to [6], wherein the antigen is a tumor antigen.

[8] The chimeric antigen receptor according to [6], wherein the extracellular domain capable of binding to an antigen is a single chain variable fragment of an antibody binding to the antigen.

[9] The chimeric antigen receptor according to [6], wherein the intracellular domain further includes a CD3ζ intracellular domain.

[10] The chimeric antigen receptor according to [9], wherein the intracellular domain of GITR is arranged on a C end side relative to the CD3ζ intracellular domain.

[11] A process for producing a chimeric antigen receptor-expressing cell, the process comprising a step of introducing the nucleic acid according to any one of [1] to [5] into a cell.

[12] The process for producing a chimeric antigen receptor-expressing cell according to [11], wherein the cell is a T cell or a cell population containing a T cell.

[13] A chimeric antigen receptor-expressing cell in which the nucleic acid according to any one of [1] to [5] is introduced.

[14] The chimeric antigen receptor-expressing cell according to [13], wherein the cell is a T cell or a cell population containing a T cell.

Effects of Invention

According to the present invention, there are provided a chimeric antigen receptor, a nucleic acid encoding a chimeric antigen receptor and a cell expressing a chimeric antigen receptor, which are useful in the field of adoptive immunity gene therapy targeting an antigen such as a tumor antigen. When the chimeric antigen receptor of the present invention is introduced into a cell, the expression amount of the chimeric antigen receptor in the cell is high and the cell exhibits a high cytotoxic activity.

BRIEF DESCRIPTION OF DRAWINGS

FIG. 2 shows the structure of a CAR used in Examples. An scFv of an antibody that bids to an antigen is shown as a "scFv", a spacer domain is shown as "Spacer domain", a transmembrane domain of CD28 is shown as "CD28 TM", an intracellular domain of CD28 is shown as "CD28 ICD", a transmembrane domain of a GITR is shown as "GITR TM", a GITR intracellular domain is shown as "GITR ICD", and a CD3ζ intracellular domain is shown as "CD3ζ". In the present specification, the structures of CDRs are respectively abbreviated as (1) z, (2) 28z, (3) z28, (4) Gz, (5) zG, (6) 28 Gz, (7) G28z, (8) zG28, (9) 28zG, and (10) z28G.

MODE FOR CARRYING OUT THE INVENTION

Figure 1:
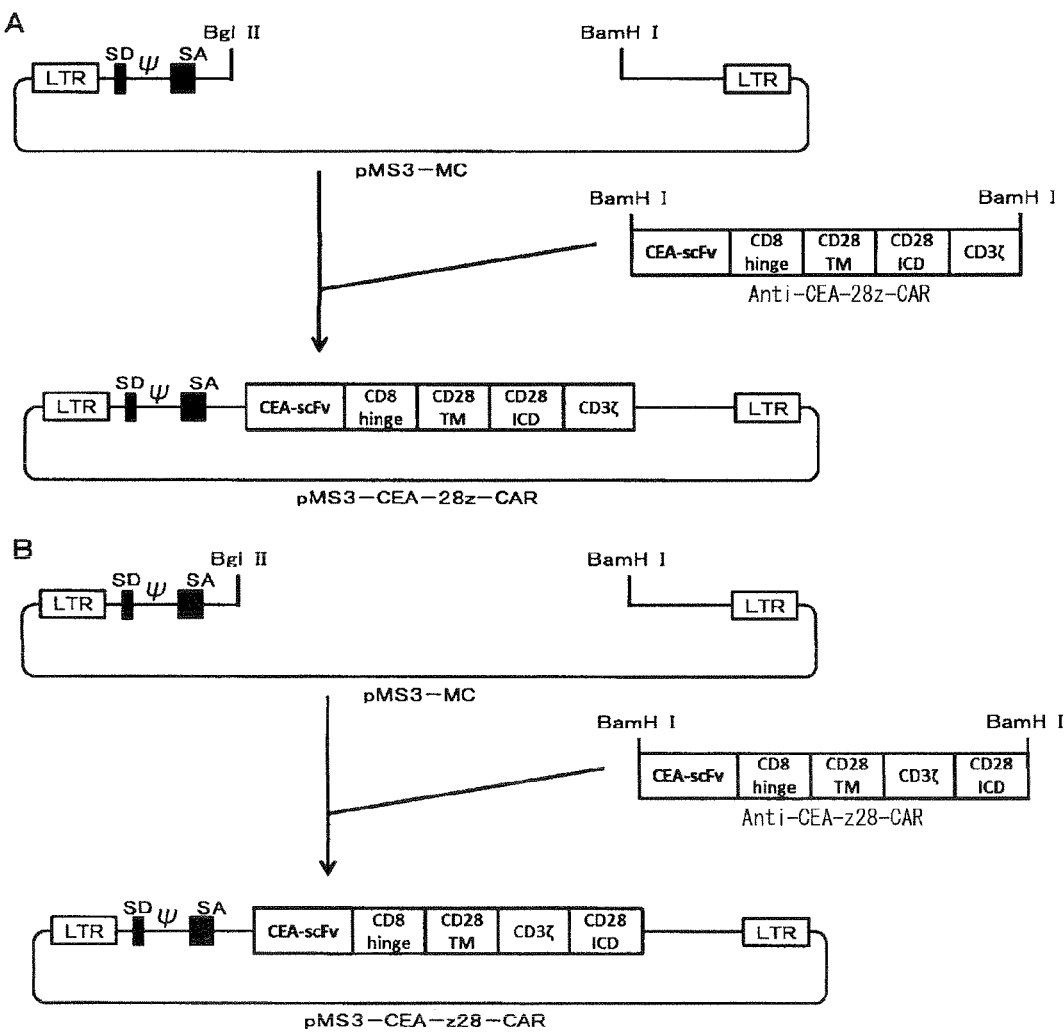
FIG. 1 shows a procedure for preparation of a CAR used in Examples. An scFv of an anti-CEA (carcinoembryonic antigen) monoclonal antibody is shown as "CEA-scFv", a hinge domain is shown as "CD8 hinge", a transmembrane domain of CD28 is shown as "CD28 TM", an intracellular domain of CD28 is shown as "CD28 ICD (IntraCellular Domain)", a CD3ζ intracellular domain is shown as "CD3ζ", a terminal repeat sequence is shown as "LTR", a splice donor sequence is shown as "SD", a splice acceptor sequence is shown as "SA", and a packaging signal sequence is shown as "ψ".

As used herein, a "chimeric antigen receptor (CAR)" means a fused protein comprising an extracellular domain capable of binding to an antigen, a transmembrane domain derived from a polypeptide different from a polypeptide from which the extracellular domain is derived, and at least one intracellular domain. The "chimeric antigen receptor (CAR)" is sometimes called a "chimeric receptor", a "T-body", or a "chimeric immune receptor (CIR)." The "extracellular domain capable of binding to an antigen" means any oligopeptide or polypeptide that can bind to a certain antigen. The "intracellular domain" means any oligopeptide or polypeptide known to function as a domain that transmits a signal to cause activation or inhibition of a biological process in a cell.

As used herein, a "tumor antigen" means a biological molecule having antigenecity, expression of which comes to be newly recognized in association with canceration of a cell. Detection, for example, immunological detection of the tumor antigen is useful in discrimination between a cancerated cell and its mother cell. The tumor antigen in the present invention includes a tumor specific antigen (an antigen which is present only in tumor cells and is not found in other normal cells), and a tumor-associated antigen (an antigen which is also present in other organs and tissues or heterogeneous and allogeneic normal cells, or an antigen which is expressed on the way of development and differentiation).

As used herein, a "glucocorticoid-induced tumor necrosis factor receptor (GITR)" means a protein that is a product of a glucocorticoid-induced tumor necrosis factor receptor-family related gene (glucocorticoid-induced TNT receptor-family related gene). The GITR is a transmembrane protein receptor on a cell surface, and is one member of a TNT receptor (TNFR) superfamily. The GITR is shown to constitutively exist on a non-activated T cell, and binds to another transmembrane protein called a GITR ligand (GITRL). The amino acid sequence of GITR is described in NCBI Reference Sequence (NCBI RefSeq): NP_004186.1, Curr. Biol., vol. 9, No. 4, pp. 215-218 (1999).

As used herein, a "single chain variable fragment (scFv)" means a single chain polypeptide derived from an antibody which retains the ability to bind to an antigen. An example of the scFv includes an antibody polypeptide which is formed by a recombinant DNA technique and in which Fv regions of immunoglobulin heavy chain (H chain) and light chain (L chain) fragments are linked via a spacer sequence. Various methods for preparing an scFv are known, and include methods described in U.S. Pat. No. 4,694,778, Science, vol. 242, pp. 423-442 (1988), Nature, vol. 334, p. 54454 (1989), and Science, vol. 242, pp. 1038-1041 (1988).

As used herein, a "domain" means one region in a polypeptide which is folded into a particular structure independently of other regions.

(1) CAR of the Present Invention

The CAR of the present invention is characterized in that it comprises an extracellular domain capable of binding to an antigen, a transmembrane domain, and at least one intracellular domain in this order from the N-terminal side, and the intracellular domain includes an intracellular domain of a GITR. The CAR of the present invention is expressed at a high level in a cell. A cell expressing the CAR of the present invention has a high proliferation rate, produces large amounts of cytokines, and has a high cytotoxic activity against a cell having, on the surface, an antigen to which a CAR binds.

(a) Extracellular Domain

The "extracellular domain capable of binding to an antigen" used for the CAR of the present invention is a domain comprising an oligopeptide or polypeptide that can bind to a target antigen, and includes, for example, an antigen-binding domain of an antibody and a ligand-binding domain of a receptor. This domain binds to and interacts with an antigen, for example, an antigen present on a cell surface, and thereby imparts specificity to a cell expressing a CAR. Particularly useful examples of the extracellular domain in the present invention include extracellular domains derived from antibodies (H chain and L chain) and variable regions of a TCR (TCRα, TCRβ, TCRγ, TCR δ), CD8α, CD8β, CD11A, CD11B, CD11C, CD18, CD29, CD49A, CD49B, CD49D, CD49E, CD49F, CD61, CD41, and CD51. The entire protein may be used effectively, and however, in particular, a domain capable of binding to an antigen or a ligand, for example, an extracellular domain of an antibody Fab fragment, an antibody variable region [V region of H chain (VH) and V region of L chain (VL)] or a receptor can be used. Particularly, a scFv can be preferably used.

The extracellular domain for the CAR of the present invention may be an extracellular domain that binds to only one antigen or ligand, or an extracellular domain that binds to two or more antigens or ligands. In addition, the present invention includes both a CAR comprising one extracellular domain and a CAR comprising two or more extracellular domains.

The extracellular domain can be selected from antibodies recognizing a target antigen or molecules interacting with the antigen. Examples of the antigen include a viral antigen, a bacterial (particularly, infectious bacterial) antigen, a parasite antigen, a cell surface marker on a target cell related to a certain condition (e.g. a tumor antigen), and a surface molecule of an immunity-related cell.

As one aspect of the present invention, there is provided a CAR capable of binding to an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus.

As another aspect of the present invention, there is provided a CAR capable of binding to an antigen derived from a bacterial strain of *Staphylococci, Streptococcus, Escherichia coli, Pseudomonas*, or *Salmonella*. Particularly, there is provided a CAR capable of binding to an antigen derived from an infectious bacterium, for example, *Helicobacter pyloris, Legionella pneumophilia*, a bacterial strain of *Mycobacteria* sps. (e.g. *M. tuberculosis, M. avium, M. intracellulare, M. kansaii,* or *M. gordonea), Staphylococcus aureus, Neisseria gonorrhoeae, Neisseria meningitides, Listeria monocytogenes, Streptococcus pyogenes*, Group A *Streptococcus*, Group B *Streptococcus (Streptococcus agalactiae), Streptococcus pneumoniae,* or *Clostridium tetani.*

As another aspect of the present invention, there is provided a CAR capable of binding to a tumor antigen such as 5T4, alpha 5β1-integrin, 707-AP, AFP, ART-4, B7H4, BAGE, β-catenin/m, Bcr-abl, MN/C IX antibody, CA125, CAMEL, CAP-1, CASP-8, CD4, CD19, CD20, CD22, CD25, CDC27/m, CD30, CD33, CD52, CD56, CD80, CDK4/m, CEA, CT, Cyp-B, DAM, EGFR, ErbB3, ELF2M, EMMPRIN, EpCam, ETV6-AML1, G250, GAGE, GnT-V, Gp100, HAGE, HER-2/new, HLA-A*0201-R170I, HPV-E7, HSP70-2M, HST-2, hTERT (or hTRT), iCE, IGF-1R, IL-2R, IL-5, KIAA0205, LAGE, LDLR/FUT, MAGE, MART-1/melan-A, MART-2/Ski, MC1R, myosin/m, MUC1, MUM-1, MUM-2, MUM-3, NA88-A, PAP, proteinase-3, p190 minor bcr-abl, Pml/RARα, PRAME, PSA, PSM, PSMA, RAGE, RU1 or RU2, SAGE, SART-1 or SART-3, survivin, TEL/AML1, TGFβ, TPI/m, TRP-1, TRP-2, TRP-2/INT2, VEGF, WT1, NY-Eso-1 or NY-Eso-B. There is also provided a CAR capable of binding to a cell surface adhesion molecule, a surface molecule of an inflammatory cell that appears in an autoimmune disease, or a TCR causing autoimmunity.

(b) Intracellular Domain

The intracellular domain used in the present invention is a molecule that can transmit a signal into a cell when the extracellular domain present within the same molecule binds to (interacts with) an antigen.

The CAR of the present invention is characterized in that it comprises an intracellular domain of a GITR as the intracellular domain. The intracellular domain of a GITR includes its variant having the same function. The term "variant" means any variant comprising substitution, deletion or addition of one or a few to plural amino acids, provided that the variant substantially retains the same function as the original sequence possesses. An example of the intracellular domain of a GITR used in the present invention includes an intracellular domain comprising amino acid numbers 193 to 241 (SEQ ID No.: 28) of a GITR (NCBI RefSeq: NP_004186.1).

For the CAR of the present invention, in addition to the intracellular domain of a GITR, an intracellular domain derived from other polypeptides can be used. Examples of such an intracellular domain include cytoplasmic sequences derived from a TCR complex and a costimulatory molecule, and any variant having the same function as those sequences.

It is known that a signal generated only via a TCR complex is insufficient to activate a T cell, and a secondary or costimulating signal is also required. Natural T cell-activation is transmitted by two different kinds of cytoplasmic signaling sequences, that is, a sequence for initiating antigen-dependent primary activation via a TCR complex (primary cytoplasmic signaling sequence) and a sequence for acting antigen-independently to provide a secondary or costimulating signal (secondary cytoplasmic signaling sequence). In a preferable aspect, the CAR of the present invention comprises the primary cytoplasmic signaling sequence and/or the secondary cytoplasmic signaling sequence as the intracellular domains.

The primary cytoplasmic signaling sequence regulates primary activation of a TCR complex. The primary cytoplasmic signaling sequence that stimulates the activation may comprise a signal transduction motif known as an immunoreceptor tyrosine-based activation motif (ITAM) [Nature, vol. 338, pp. 383-384 (1989)]. On the other hand, the primary cytoplasmic signaling sequence that acts in an inhibitory way comprises a signal transduction motif known as an immunoreceptor tyrosine-based inhibition motif (ITIM) [J Immunol., vol. 162, No. 2, pp. 897-902 (1999)]. In the present invention, an intracellular domain having an ITAM or an ITIM can be used.

Examples of the intracellular domain having an ITAM that can be used in the present invention include intracellular domains having ITAM derived from CD3ζ, FcRγ, FcRβ, CD3γ, CD3 δ, CD3ε, CD5, CD22, CD79a, CD79b, and CD66d. Specifically, examples of the ITAM include peptides having sequences of amino acid numbers 51 to 164 (SEQ ID No.: 26) of CD3ζ (NCBI RefSeq: NP_932170.1), amino acid numbers 45 to 86 of FcεRIγ (NCBI RefSeq: NP_004097.1), amino acid numbers 201 to 244 of FcεRIβ (NCBI RefSeq: NP_000130.1), amino acid numbers 139 to 182 of CD3γ (NCBI RefSeq: NP_000064.1), amino acid numbers 128 to 171 of CD3 δ (NCBI RefSeq: NP_000723.1), amino acid numbers 153 to 207 of CD3ε (NCBI RefSeq: NP_000724.1), amino acid numbers 402 to 495 of CD5 (NCBI RefSeq: NP_055022.2), amino acid numbers 707 to 847 of 0022 (NCBI RefSeq: NP_001762.2), amino acid numbers 166 to 226 of CD79a (NCBI RefSeq: NP_001774.1), amino acid numbers 182 to 229 of CD79b (NCBI RefSeq: NP_000617.1), and amino acid numbers 177 to 252 of CD66d (NCBI RefSeq: NP_001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein.

Examples of the intracellular domain comprising a secondary cytoplasmic signaling sequence that can be used in the present invention include sequences derived from CD2, CD4, CD5, CD8α, CD8β, CD28, CD134, CD137, ICOS, and CD154. Specific examples thereof include peptides having sequences of amino acid numbers 236 to 351 of CD2 (NCBI RefSeq: NP_001758.2), amino acid numbers 421 to 458 of CD4 (NCBI RefSeq: NP_000607.1), amino acid numbers 402 to 495 of CD5 (NCBI RefSeq: NP_055022.2), amino acid numbers 207 to 235 of CD8α (NCBI RefSeq: NP_001759.3), amino acid numbers 196 to 210 of CD83 (GenBank: AAA35664.1), amino acid numbers 181 to 220 (SEQ ID No.: 25) of CD28 (NCBI RefSeq: NP_006130.1), amino acid numbers 214 to 255 of CD137 (4-1BB, NCBI RefSeq: NP_001552.2), amino acid numbers 241 to 277 of CD134 (OX40, NCBI RefSeq: NP_003318.1), and amino acid numbers 166 to 199 of ICOS (NCBI RefSeq: NP_036224.1), and their variants having the same function as these peptides have.

The present invention includes a CAR comprising only an intracellular domain of a GITR as the intracellular domain, and a CAR comprising one or more, for example, 2 or intracellular domains in addition to the intracellular domain of a GITR. Particularly preferred examples include a CAR comprising an intracellular domain of a GITR and an intracellular domain of CD3ζ as the intracellular domains, and a CAR comprising an intracellular domain of a GITR, an intracellular domain of CD3ζ and an intracellular domain of CD28 as the intracellular domains. The present invention also includes a CAR comprising two or more same intracellular domains which are linked tandemly. In one aspect, the present invention provides a CAR in which an intracellular domain of a GITR is arranged on a C-terminal side relative to an intracellular domain of CD3ζ, that is, a CAR comprising an intracellular domain of CD3ζ and an intracellular domain of a GITR which are linked in this order from the N-terminal side. The present invention also includes CARs obtained by further adding an intracellular domain of CD28 to the aforementioned CAR, that is, a CAR comprising an intracellular domain of CD28, an intracellular domain of CD3ζ, and an intracellular domain of a GITR which are linked in this order from the N-terminal side, and a CAR comprising an intracellular domain of CD3ζ, an intracellular domain of a GITR, and an intracellular domain of CD28 which are linked in this order from the N-terminal side. As another aspect, the present invention also includes a CAR in which an intracellular domain of a GITR is arranged on a C-terminal side.

In a CAR comprising a plurality of intracellular domains, an oligopeptide linker or a polypeptide linker can be inserted between the intracellular domains to link the domains. Preferably, a linker having a length of 2 to 10 amino acids can be used. Particularly, a linker having a glycine-serine continuous sequence can be used.

(c) Transmembrane Domain and Spacer Domain

The CAR of the present invention comprises a transmembrane domain. The transmembrane domain may be derived from a natural polypeptide, or may be artificially designed. The transmembrane domain derived from a natural polypeptide can be obtained from any membrane-binding or transmembrane protein. For example, a transmembrane domain of a T cell receptor α or β chain, a CD3ζ chain, CD28, CD3ε, CD45, CD4, CD5, CD8, CD9, CD16, CD22, CD33, CD37, CD64, CD80, CD86, CD134, CD137, ICOS, CD154, or a GITR can be used. The artificially designed transmembrane domain is a polypeptide mainly comprising hydrophobic residues such as leucine and valine. It is preferable that a triplet of phenylalanine, tryptophan and valine is found at each end of the synthetic transmembrane domain. Optionally, a short oligopeptide linker or a polypeptide linker, for example, a linker having a length of 2 to 10 amino acids can be arranged between the transmembrane domain and the intracellular domain as described in the above (b). Particularly, a linker sequence having a glycine-serine continuous sequence can be used.

As one aspect of the present invention, a transmembrane domain having a sequence of amino acid numbers 153 to 180 (SEQ ID No.: 24) of CD28 (NCBI RefSeq: NP_006130.1) can be used as the transmembrane domain. As another aspect, a transmembrane domain having a sequence of amino acid numbers 162 to 183 (SEQ ID No.: 27) of a GITR (NCBI RefSeq: NP_004186.1) can be used.

In the CAR of the present invention, a spacer domain can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 118 to 178 (SEQ ID No.: 23) which is a hinge region of CD8α (NCBI RefSeq: NP_001759.3), amino acid numbers 135 to 195 of CD8β (GenBank: AAA35664.1), amino acid numbers 315 to 396 of CD4 (NCBI RefSeq: NP_000607.1), or amino acid numbers 137 to 152 of CD28 (NCBI RefSeq: NP_006130.1) can be used. Also, as the spacer domain, a part of a constant region of an antibody H chain or L chain (CH1 region or CL region, for example, a peptide having an amino acid sequence shown in SEQ ID No.: 34) can be used. Further, the spacer domain may be an artificially synthesized sequence.

The CAR of the present invention can be designed so as to form a polymer, particularly, a dimer. For example, cysteine is inserted into the spacer domain and/or the transmembrane domain to polymerize (dimerize) the CAR.

Further, in the CAR of the present invention, a signal peptide sequence can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR of the present invention.

(2) Nucleic Acid Encoding CAR

The present invention provides a nucleic acid encoding the CAR described in the above (1). The nucleic acid encoding the CAR can be easily prepared from an amino acid sequence of the specified CAR by a conventional method. A base sequence encoding an amino acid sequence can be obtained from the aforementioned NCBI RefSeq IDs or accession numbers of GenBenk for an amino acid sequence of each domain, and the nucleic acid of the present invention can be prepared using a standard molecular biological and/or chemical procedure. For example, based on the base sequence, a nucleic acid can be synthesized, and the nucleic acid of the present invention can be prepared by combining DNA fragments which are obtained from a cDNA library using a polymerase chain reaction (PCR).

The nucleic acid of the present invention can be linked to another nucleic acid so as to be expressed under control of a suitable promoter. Examples of the promoter include a promoter that constitutively promotes the expression of a gene, a promoter that induces the expression of a gene by the action of a drug or the like (e.g. tetracycline or doxorubicin). The nucleic acid of the present invention can be also linked to, in order to attain efficient transcription of the nucleic acid, other regulatory elements that cooperate with a promoter or a transcription initiation site, for example, a nucleic acid comprising an enhancer sequence or a terminator sequence. In addition to the nucleic acid of the present invention, a gene that can be a marker for confirming expression of the nucleic acid (e.g. a drug resistance gene, a gene encoding a reporter enzyme, or a gene encoding a fluorescent protein) may be incorporated.

The present invention provides a composition comprising the nucleic acid of the present invention as an active ingredient, together with a pharmaceutically acceptable excipient. Suitable pharmaceutically acceptable excipients are well known to a person skilled in the art. Examples of the pharmaceutically acceptable excipients include phosphate buffered saline (e.g. 0.01 M phosphate, 0.138 M NaCl, 0.0027 M KCl, pH 7.4), an aqueous solution containing a mineral acid salt such as a hydrochloride, a hydrobromide, a phosphate, or a sulfate, saline, a solution of glycol or ethanol, and a salt of an organic acid such as an acetate, a propionate, a malonate or a benzoate. An adjuvant such as a wetting agent or an emulsifier, and a pH buffering agent can also be used. As the pharmaceutically acceptable excipients, excipients described in Remington's Pharmaceutical Sciences (Mack Pub. Co., N.J. 1991) (which is incorporated herein by reference) can be appropriately used. The composition of the present invention can be formulated into a known form suitable for parenteral administration, for example, injection or infusion. Further, the composition of the present invention may comprise formulation additives such as a suspending agent, a preservative, a stabilizer and/or a dispersant, and a preservation agent for extending a validity term during storage. The composition may be in a dry form for reconstitution with an appropriate sterile liquid prior to use. For fine particle-mediated administration, a particle such as a gold particle of a microscopic size can be coated with a DNA.

When the nucleic acid of the present invention is introduced into a cell ex vivo, the nucleic acid of the present invention may be combined with a substance that promotes transference of a nucleic acid into a cell, for example, a reagent for introducing a nucleic acid such as a liposome or a cationic lipid, in addition to the aforementioned excipients. Alternatively, a vector carrying the nucleic acid of the present invention is also useful as described later. Particularly, a composition in a form suitable for administration to a living body which contains the nucleic acid of present invention carried by a suitable vector is suitable for in vivo gene therapy.

A composition comprising the nucleic acid of the present invention as an active ingredient can be administered for treatment of, for example, a cancer [blood cancer (leukemia), solid tumor etc.], an inflammatory disease/autoimmune disease (asthma, eczema), hepatitis, and an infectious disease the cause of which is a virus such as influenza and HIV, a bacterium, or a fungus, for example, a disease such as tuberculosis, MRSA, VRE, or deep mycosis, depending on an antigen to which a CAR encoded by the nucleic acid binds. A composition comprising the nucleic acid of the present invention as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not particularly limited.

(3) Process for Producing Cell Expressing CAR

A process for producing a cell expressing the CAR of the present invention includes a step of introducing the nucleic acid encoding a CAR described in the above (2) into a cell. The step is carried out ex vivo. For example, a cell can be transformed ex vivo with a virus vector or a non-virus vector carrying the nucleic acid of the present invention to produce a cell expressing the CAR of the present invention.

In the process of the present invention, a cell derived from a mammal, for example, a human cell, or a cell derived from a non-human mammal such as a monkey, a mouse, a rat, a pig, a horse, or a dog can be used. The cell used in the process of the present invention is not particularly limited, and any cell can be used. For example, a cell collected, isolated, purified or induced from a body fluid, a tissue or an organ such as blood (peripheral blood, umbilical cord blood etc.) or bone marrow can be used. A peripheral blood mononuclear cell (PBMC), an immune cell [a dendritic cell, a B cell, a hematopoietic stem cell, a macrophage, a monocyte, a NK cell or a hematopoietic cell (a neutrophil, a basophil)], an umbilical cord blood mononuclear cell, a fibroblast, a precursor adipocyte, a hepatocyte, a skin keratinocyte, a mesenchymal stem cell, an adipose stem cell, various cancer cell strains, or a neural stem cell can be used. In the present invention, particularly, use of a T cell, a precursor cell of a T cell (a hematopoietic stem cell, a lymphocyte precursor cell etc.) or a cell population containing them is preferable. Examples of the T cell include a CD8-positive T cell, a CD4-positive T cell, a regulatory T cell, a cytotoxic T cell, and a tumor infiltrating lymphocyte. The cell population containing a T cell and a precursor cell of a T cell includes a PBMC. The aforementioned cells may be collected from a living body, obtained by expansion culture of a cell collected from a living body, or established as a cell strain. When transplantation of the produced CAR-expressing cell or a cell differentiated from the produced CAR-expressing cell into a living body is desired, it is preferable to introduce the nucleic acid into a cell collected from the living body itself or a conspecific living body thereof.

The nucleic acid encoding the CAR of the present invention can be inserted into a vector, and the vector can be introduced into a cell. For example, a virus vector such as a retrovirus vector (including an oncoretrovirus vector, a lentivirus vector, and a pseudo type vector), an adenovirus vector, an adeno-associated virus (AAV) vector, a simian virus vector, a vaccinia virus vector or a sendai virus vector, an Epstein-Barr virus (EBV) vector, and a HSV vector can be used. As the virus vector, a virus vector lacking the replicating ability so as not to self-replicate in an infected cell is preferably used.

In addition, a non-virus vector can also be used in the present invention in combination with a liposome and a condensing agent such as a cationic lipid as described in WO 96/10038, WO 97/18185, WO 97/25329, WO 97/30170 and WO 97/31934 (which are incorporated herein by reference). The nucleic acid of the present invention can be also introduced into a cell by calcium phosphate transduction, DEAE-dextran, electroporation, or particle bombardment.

For example, when a retrovirus vector is used, the process of the present invention can be carried out by selecting a suitable packaging cell based on a LTR sequence and a packaging signal sequence possessed by the vector and preparing a retrovirus particle using the packaging cell. Examples of the packaging cell include PG13 (ATCC CRL-10686), PA317 (ATCC CRL-9078), GP+E-86 and GP+envAm-12 (U.S. Pat. No. 5,278,056), and Psi-Crip [Proceedings of the National Academy of Sciences of the United States of America, vol. 85, pp. 6460-6464 (1988)]. A retrovirus particle can also be prepared using a 293 cell or a 293T cell having high transfection efficiency. Many kinds of retrovirus vectors produced based on retroviruses and packaging cells that can be used for packaging of the retrovirus vectors are widely commercially available from many companies.

In the step of introducing a nucleic acid into a cell, a functional substance for improving the introduction efficiency can also be used [e.g. WO 95/26200 and WO 00/01836 (which are incorporated herein by reference)]. Examples of the substance for improving the introduction efficiency include a substance having ability to bind to a virus vector, for example, fibronectin and a fibronectin fragment. Preferably, a fibronectin fragment having a heparin binding site, for example, a fragment commercially available as RetroNetcin (registered trademark, CH-296, manufactured by TAKARA BIC INC.) can be used. Also, polybrene which is a synthetic polycation having an effect of improving the efficiency of infection of a retrovirus into a cell, a fibroblast growth factor, V type collagen, polylysine or DEAE-dextran can be used.

In a preferable aspect of the present invention, the functional substance can be used in a state of being immobilized on a suitable solid phase, for example, a container used for cell culture (plate, petri dish, flask or bag) or a carrier (microbeads etc.).

(4) Cell Expressing CAR

The cell expressing the CAR of the present invention is a cell in which the nucleic acid encoding a CAR described in the above (2) is introduced and expressed by the production process described in the above (3).

The cell of the present invention binds to a specific antigen via the CAR, thereby a signal is transmitted into the cell, and as a result, the cell is activated. The activation of the cell expressing the CAR is varied depending on the kind of a host cell and an intracellular domain of the CAR, and can be confirmed based on, for example, release of a cytokine, improvement of a cell proliferation rate, change in a cell surface molecule, or the like as an index. For example, release of a cytotoxic cytokine (a tumor necrosis factor, lymphotoxin, etc.) from the activated cell causes destruction of a target cell expressing an antigen. In addition, release of a cytokine or change in a cell surface molecule stimulates other immune cells, for example, a B cell, a dendritic cell, a NK cell, and a macrophage.

The cell expressing the CAR can be used as a therapeutic agent for a disease. The therapeutic agent comprises the cell expressing the CAR as an active ingredient, and may further comprise a suitable excipient. Examples of the excipient include the aforementioned pharmaceutically acceptable excipients for the composition comprising the nucleic acid of the present invention as an active ingredient, various cell culture media, and isotonic sodium chloride. The disease against which the cell expressing the CAR is administered is not particularly limited as long as the disease shows sensitivity to the cell. Examples of the disease include a cancer [blood cancer (leukemia), solid tumor etc.], an inflammatory disease/autoimmune disease (asthma, eczema), hepatitis, and an infectious disease, the cause of which is a virus such as influenza and HIV, a bacterium, or a fungus, for example, tuberculosis, MRSA, VRE, and deep mycosis. The cell expressing the CAR of the present invention that binds to an antigen possessed by a cell that is desired to be decreased or eliminated for treatment of the aforementioned diseases, that is, a tumor antigen, a viral antigen, a bacterial antigen or the like is administered for treatment of these diseases. The cell of the present invention can also be utilized for prevention of an infectious disease after bone marrow transplantation or exposure to radiation, donor lymphocyte transfusion for the purpose of remission of recurrent leukemia, and the like. The therapeutic agent comprising the cell expressing the CAR as an active ingredient can be administered intradermally, intramuscularly, subcutaneously, intraperitoneally, intranasally, intraarterially, intravenously, intratumorally, or into an afferent lymph vessel, by parenteral administration, for example, by injection or infusion, although the administration route is not limited.

EXAMPLES

The present invention is explained more specifically below by way of Examples, but the present invention is not limited to the following Examples.

Among procedures described herein, fundamental procedures were carried out according to the methods described in Molecular Cloning: A Laboratory Manual 3rd ed., edited by T. Maniatis et al., published by Cold Spring Harbor Laboratory in 2001 (which is incorporated herein by reference).

Example 1

Preparation of Anti-CEA-CAR Expression Vector

First, PCR was performed with a 3MSCV5 primer shown in SEQ ID NO: 1 and a 3MSCV3 primer shown in SEQ ID NO: 2 using pMSCVneo (manufactured by Clontech) as a template, to amplify a MSCV3' LTR site. The amplified fragment thus obtained was cut with restriction enzymes XhoI and EcoRI, and cloned into a XhoI-EcoRI site of a pM vector [pM vector described in Gene Therapy vol. 7, pp. 797-804 (2000)] to prepare pMS-MC. Further, a pMEI-5 vector (manufactured by TAKARA BIO INC.) was cut with restriction enzymes MluI and XhoI, and inserted into a MluI-XhoI site of the pMS-MC to prepare pMS3-MC. The pMS3-MC contains 5'LTR derived from MMLV, SD derived from MMLV, ψ derived from MMLV, SA derived from a human EF1α gene, and 3'LTR consisting of a U3 region derived from MSCV and the other regions derived from MMLV, in this order from the 5' end.

As shown in FIGS. 1A and 1B, an artificial synthetic gene of a base sequence shown in SEQ ID NO: 3 (in FIG. 1A, referred to as anti-CEA-28z-CAR) and an artificial synthetic gene of a base sequence shown in SEQ ID NO: 4 (in FIG. 1B, referred to as anti-CEA-z28-CAR) were prepared. These artificial synthetic genes encode one molecule of a chimeric protein consisting of a scFv (the amino acid sequence of which is shown in SEQ ID NO: 22) of an anti-CEA monoclonal antibody which binds to a cancer antigen CEA (carcinoembryonic antigen), a CD8α chain hinge domain having an amino acid sequence shown in SEQ ID NO: 23, a CD28 transmembrane domain having an amino acid sequence shown in SEQ ID NO: 24, a CD28 intracellular domain having an amino acid sequence shown in SEQ ID NO: 25, and a CD3ζ intracellular domain having an amino acid sequence shown in SEQ ID NO: 26. In FIG. 1, a scFv of an anti-CEA monoclonal antibody is referred to as "CEA-scFv", a hinge domain is referred to as "CD8 hinge", a transmembrane domain is referred to as "CD28 TM", an intracellular domain of CD28 is referred to as "CD28 ICD (IntraCellular Domain)", a CD3ζ intracellular domain is referred to as "CD3ζ", a terminal repeat sequence is referred to as "LTR", a splice donor sequence is referred to as "SD", a splice acceptor sequence is referred to as "SA", and a packaging signal sequence is referred to as "ψ". Nucleic acid fragments comprising these artificial synthetic genes were cloned into pMS3-MC vectors digested with BglII-BamHI, to prepare a pMS3-CEA-28z-CAR vector expressing a CAR in which the CD28 intracellular domain is arranged on an N-terminal side relative to the CD3ζ intracellular domain and a pMS3-CEA-z28-CAR vector expressing a CAR in which the CD3ζ intracellular domain is arranged on an N-terminal side relative to the CD28 intracellular domain.

Example 2

Preparation of CAR Expression Vector Carrying GITR Gene

An artificial synthetic gene shown in SEQ ID NO: 5 was prepared. This artificial synthetic gene encodes a GITR transmembrane domain having an amino acid sequence shown in SEQ ID NO: 27 and a GITR intracellular domain having an amino acid sequence shown in SEQ ID NO: 28. Using this artificial synthetic gene as a template, PCR was performed with a 28TM-G-F primer shown in SEQ ID NO: 6 and a G-z-R primer shown in SEQ ID NO: 7 to obtain an amplified DNA fragment A, PCR was performed using with a z-G-F primer shown in SEQ ID NO: 8 and a G-MC-R primer shown in SEQ ID NO: 9 to obtain an amplified DNA fragment B, PCR was performed with a 28SD-G-F primer shown in SEQ ID NO: 10 and a G-z-R primer shown in SEQ ID NO: 7 to obtain an amplified DNA fragment C, PCR was performed with a hinge-G-F primer shown in SEQ ID NO: 11 and a G-28SD-R primer shown in SEQ ID NO: 12 to obtain an amplified DNA fragment D, and PCR was performed with a z-G-F primer shown in SEQ ID NO: 8 and a G-28SD-R2 primer shown in SEQ ID NO: 13 to obtain an amplified DNA fragment E.

Using the pMS3-CEA-28z-CAR vector prepared in Example 1 as a template, PCR was performed with a 28TM-R primer shown in SEQ ID NO: 14 and a z-F primer shown in SEQ ID NO: 15. Into the amplification product thus obtained was cloned the amplified DNA fragment A using In-Fusion Advantage PCR Cloning Kit (manufactured by Clontech) to prepare a pMS3-CEA-Gz-CAR vector.

Similarly, using the pMS3-CEA-z28-CAR vector prepared in Example 1 as a template, PCR was performed with a z-R primer shown in SEQ ID NO: 16 and an END-MC-F primer shown in SEQ ID NO: 17. Into the amplification product thus obtained was cloned the amplified DNA fragment B to prepare a pMS3-CEA-zG-CAR vector. An amino acid sequence of CEA-zG-CAR expressed by this vector is shown in SEQ ID NO: 29.

Using the pMS3-CEA-28z-CAR vector as a template, PCR was performed with a 28SD-R primer shown in SEQ ID NO: 18 and a z-F primer shown in SEQ ID NO: 15. Into the amplification product thus obtained was cloned the amplified DNA fragment C to prepare a pMS3-CEA-28 Gz-CAR vector.

Using the pMS3-CEA-28z-CAR vector as a template, PCR was performed with a hinge-R primer shown in SEQ ID NO: 19 and a 28SD-F primer shown in SEQ ID NO: 20. Into the amplification product thus obtained was cloned the amplified DNA fragment D to prepare a pMS3-CEA-G28z-CAR vector.

Using the pMS3-CEA-z28-CAR vector as a template, PCR was performed with a z-R primer shown in SEQ ID NO: 16 and a 28SD-F2 primer shown in SEQ ID NO: 21. Into the amplification product thus obtained was cloned the amplified DNA fragment E to prepare a pMS3-CEA-zG28-CAR vector. An amino acid sequence of CEA-zG28-CAR expressed by this vector is shown in SEQ ID NO: 30.

Using the pMS3-CEA-28z-CAR vector as a template, PCR was performed with a z-R primer shown in SEQ ID NO: 16 and an END-MC-F primer shown in SEQ ID NO: 17. Into the amplification product thus obtained was cloned the amplified DNA fragment B to prepare a pMS3-CEA-28zG-CAR vector.

The structures of CARs expressed by the prepared vectors respectively correspond to the structures (2) to (9) shown in FIG. 2. That is, the pMS3-CEA-28z-CAR vector expresses a CAR having the structure of (2) 28z, the pMS3-CEA-z28-CAR vector expresses a CAR having the structure of (3) z28, the pMS3-CEA-Gz-CAR vector expresses a CAR having the structure of (4) Gz, the pMS3-CEA-zG-CAR vector expresses a CAR having the structure of (5) zG, the pMS3-CEA-28 Gz-CAR vector expresses a CAR having the structure of (6) 28 Gz, the pMS3-CEA-G28z-CAR vector expresses a CAR having the structure of (7) G28z, the pMS3-CEA-zG28-CAR vector expresses a CAR having the structure of (8) zG28, and the pMS3-CEA-28zG-CAR vector expresses a CAR having the structure of (9) 28zG.

Example 3

Preparation of Retrovirus Solution

*Escherichia coli* JM109 was transformed with the plasmid vectors prepared in Examples 1 and 2 to obtain transformants. Plasmid DNAs harbored by these transformants were purified using QIAGEN Plasmid Midi Kit (manufactured by Qiagen), and subjected to the following steps as DNAs for transfection.

The DNA for transfection thus prepared, and a pGP vector and a pEeco vector contained in Retrovirus Packaging Kit Eco (manufactured by TAKARA BIO INC.) were transfected into a 293T cell. This manipulation was performed according to the product protocol of the kit. From each of the transformed cells thus obtained, a supernatant containing an ecotropic virus was obtained, and filtered with a 0.45 μm filter (Milex HV, manufactured by Millipore). Using this supernatant, a PG13 cell (ATCC CRL-10686) was infected with the ecotropic virus by a method using polybrene. A culture supernatant of the cell thus obtained was recovered, and filtered with a 0.45 μm filter to obtain a retrovirus solution for expression of anti-CEA-CAR. The respective viruses were named (2) CEA-28z, (3) CEA-z28, (4) CEA-Gz, (5) CEA-zG, (6) CEA-28 Gz, (7) CEA-G28z, (8) CEA-zG28, and (9) CEA-28zG, from the structures of CARs expressed by the viruses.

Example 4

Infection of Anti-CEA-CAR Retrovirus into Human PBMC-1

A peripheral blood mononuclear cell (PBMC) separated from human peripheral blood which had been collected after obtaining informed consent was infected two times with each retrovirus solution for expression of anti-CEA-CAR prepared in Example 3 by a standard method using RetroNectin (registered trademark, manufactured by TAKARA BIO INC.) to prepare a PBMC expressing each anti-CEA-CAR. For each retrovirus solution, three groups of PBMCs were prepared, and infection was carried out using 3 serial dilutions (2-fold, 4-fold and 8-fold dilutions) of the retrovirus solution. Five days after the second virus infection, a genome DNA was extracted from the infected cell using FastPure DNA Kit (manufactured by TAKARA BIO INC.). The number of copies of the retrovirus incorporated into the genome was measured using Provirus Copy Number Detection Primer Set, Human (manufactured by TAKARA BIO INC.) and CycleavePCR Core Kit (manufactured by TAKARA BIO INC.).

Figure 3:
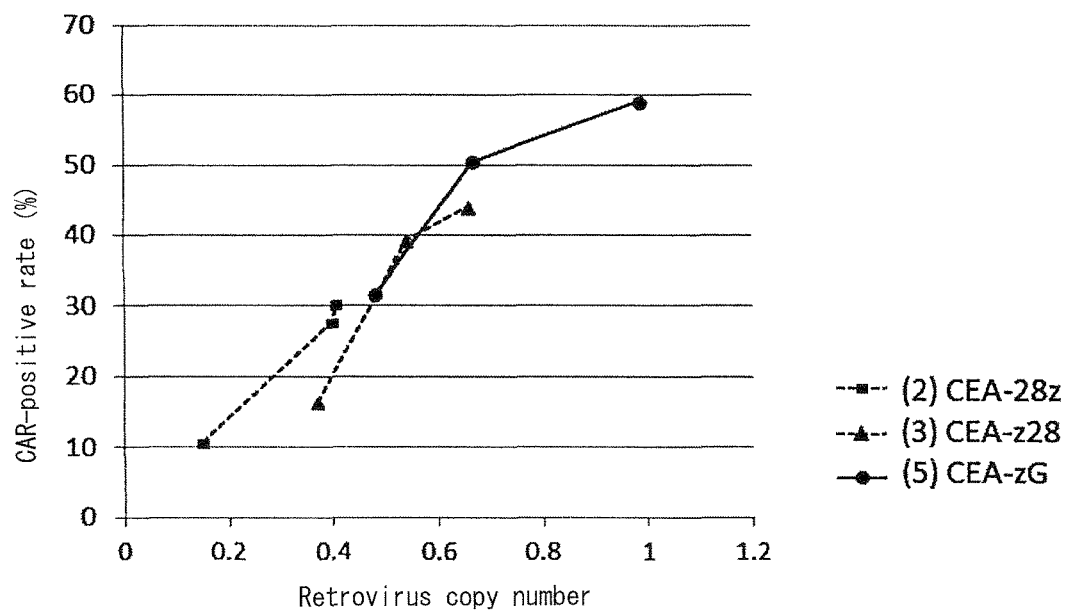
FIG. 3 shows rates of binding of CEA to CAR-introduced cells, relative to retrovirus copy numbers.
Figure 4:
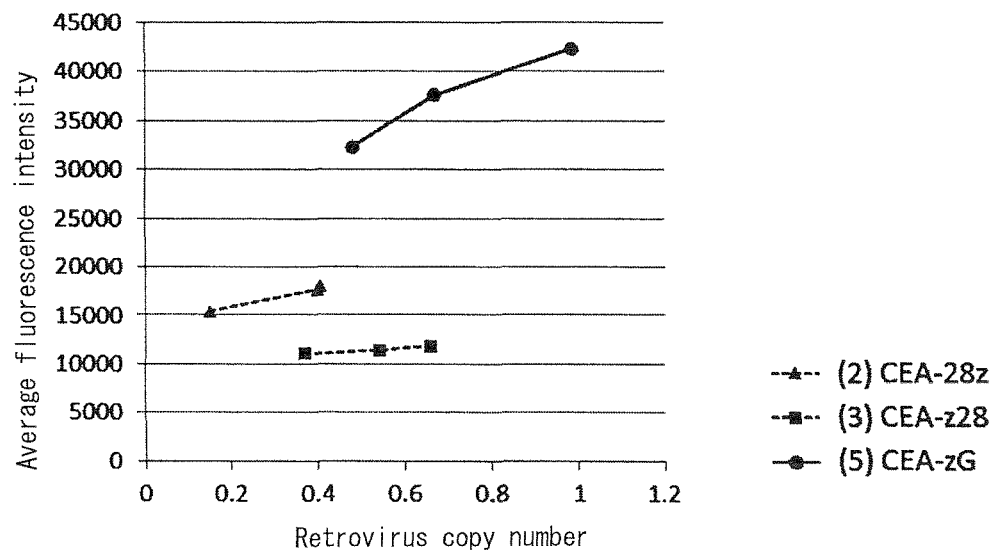
FIG. 4 shows fluorescence intensities of labeled CEA binding to CAR-introduced cells, relative to retrovirus copy numbers.

In addition, 3 days after the second virus infection, a CEA protein that had been labeled with biotin using Biotin-Labeling Kit-NH$_2$ (manufactured by DOJINDO LABORATORIES) was added to the infected cell, followed by staining with streptavidin-PE (phycoerythrin: manufactured by Becton Dickinson) and a FITC-labeled anti-Human CD8 antibody (manufactured by Becton Dickinson). Using a flow cytometer, the stained cells were subjected to measurement of a rate of PE-positive cells in FITC-positive cells, that is, a rate of cells positive for CAR that binds to CEA in CD8-positive cells. In addition, an average fluorescence intensity of the fluorescent dye PE was measured. The average fluorescence intensity reflects the expression amount of anti-CEA-CAR in an anti-CEA-CAR-positive cell. As a result, it was confirmed that the CARs on the cell surfaces were positive in the all cells. Particularly, the cell infected with (5) CEA-zG had a higher positive rate of anti-CEA-CAR and a higher average fluorescence intensity than the cell infected with (4) CEA-Gz. Regarding the cells infected with (2) CEA-28z, (3) CEA-z28, and (5) CEA-zG, a relationship between the anti-CEA-CAR-positive rate (ordinate axis) and the number of copies of the retrovirus incorporated into the genome (abscissa axis) is shown in FIG. 3, and a relationship between the average fluorescence intensity of PE derived from the cell positive for the biotin-labeled CEA protein (ordinate axis) and the number of copies of the retrovirus incorporated into the genome (abscissa axis) are shown in FIG. 4. As shown in FIG. 3 and FIG. 4, it was found that the PBMC in which anti-CEA-zG-CAR was introduced [(5) CEA-zG] had a higher anti-CEA-CAR-positive rate and also a higher expression amount of anti-CEA-CAR, as compared with the other anti-CEA-CAR-introduced PBMCs that did not have a GITR intracellular domain.

Example 5

Infection of Anti-CEA-CAR Retrovirus into Human PBMC-2

Figure 5:
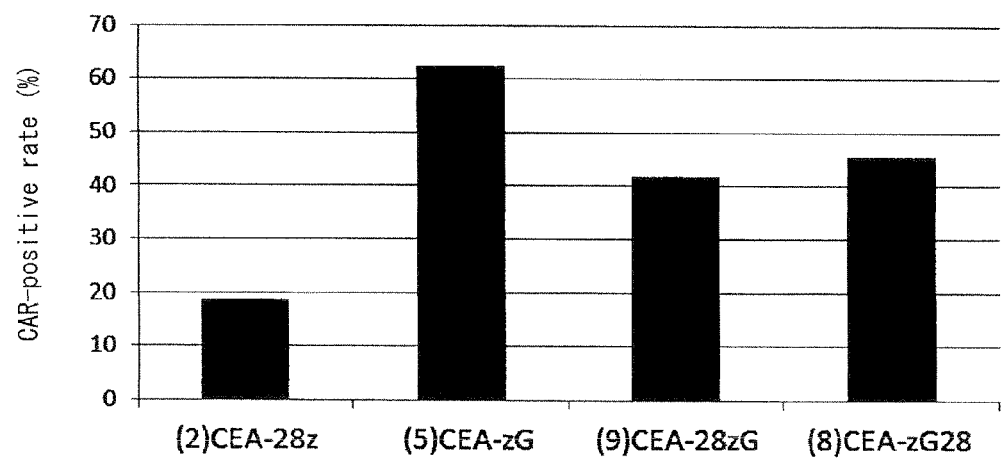
FIG. 5 shows rates of binding of CEA in CAR-introduced cells.
Figure 6:
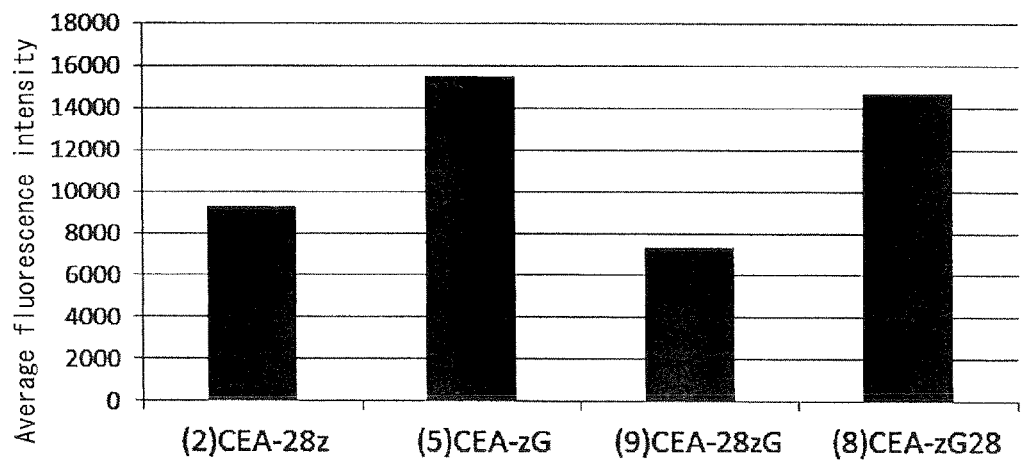
FIG. 6 shows fluorescence intensities of labeled CEA binding to CAR-introduced cells.

A human PBMC which had been collected after obtaining informed consent was infected two times with, of the retrovirus solutions for expression of anti-CEA-CAR prepared in Example 3, a 4-fold, 6-fold or 8-fold dilution of (2) CEA-28z, an undiluted solution or a 2-fold or 4-fold dilution of (5) CEA-zG, or a 2-fold, 4-fold or 8-fold dilution of (9) CEA-28zG or (8) CEA-zG28 by a standard method using RetroNectin (registered trademark, manufactured by TAKARA BIO INC.) to prepare a PBMC expressing each anti-CEA-CAR. Six days after the second virus infection, the infected cells were recovered and the number of copies of the virus incorporated into the genome was measured in the same manner as Example 4. Anti-CEA-CAR-expressing cells having relatively close retrovirus copy numbers [(2) CEA-28z: 0.27 copy, (5) CEA-zG: 1.3 copies, (9) CEA-28zG: 0.81 copy, (8) CEA-zG28: 0.65 copy] were selected, and then stained and subjected to measurement of a rate of cells positive for anti-CEA-CAR in CD8-positive cells and an average fluorescence intensity of PE in the same manner as Example 4. FIG. 5 shows positive rates of anti-CEA-CAR, and FIG. 6 shows PE average fluorescence intensities of the positive cells. As shown in FIG. 5 and FIG. 6, it was found that the cells infected with (5) CEA-zG, (9) CEA-28zG and (8) zG28 had a higher rate of cells expressing anti-CEA-CAR and also a higher expression amount of anti-CEA-CAR, as compared with the cell infected with (2) CEA-28z.

In addition, 11 days after the second virus infection, the infected cells were recovered and subjected to measurement of cytotoxic activity on a 96-well plate by Calsein release assay. After Calsein-AM (manufactured by DOJINDO LABORATORIES) was incorporated into CEA-positive cell strain MKN-45 and CEA-negative cell strain MKN-1 (both are available from RIKEN BioResource Center), $1.0 \times 10^5$ cells/mL suspensions of the cell strains were added in an amount of 100 μL per well. In addition, the anti-CEA-CAR-introduced PBMCs as described above, and a PBMC in which a vector had not been introduced (NGMC) as a control were suspended, and 100 μL of the suspension was added to the well so that the ET ratio became 30, 10, 3 or 1. A well to which 100 μL of a medium as a Low control, or 100 μL of 0.1% Triton X-100 as a High control was added in place of a PBMC was prepared. After the cells and controls were prepared, the 96-well plate was incubated at 37° C. for 4 hours in a $CO_2$ incubator equilibrated with a 5.0% $CO_2$ gas. Then, 100 μL of the supernatant was subjected to measurement of a fluorescence intensity at $\lambda_{ex}$=490 nm and $\lambda_{em}$515 nm, and the amount of released Calsein was measured. Cytotoxic activity (Lysis) is calculated by the following equation, and results are shown in FIG. 7.

Cytotoxic activity(%)=100×(measured value of each well−measured value of Low control)/(measured value of High control−measured value of Low control)

Figure 7:
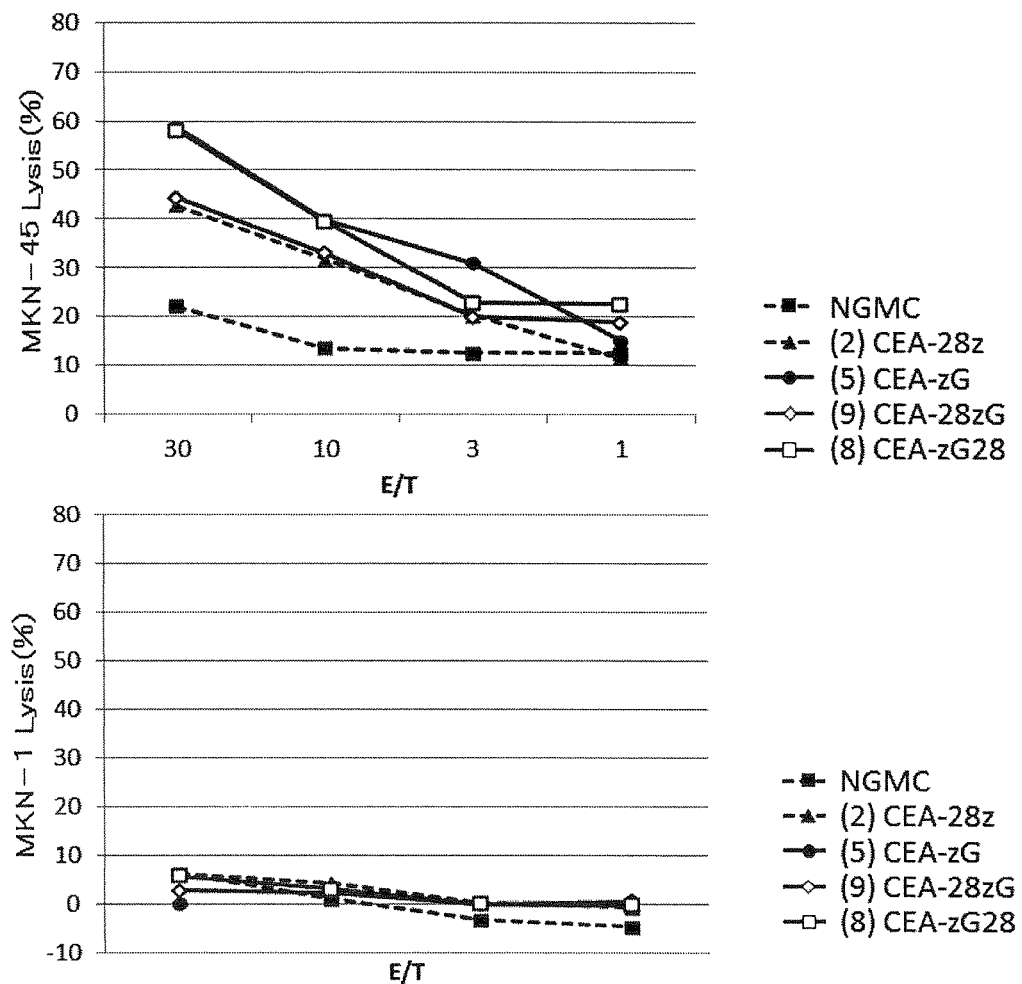
FIG. 7 shows cytotoxic activities of CAR-introduced cells.

As shown in FIG. 7, cytotoxic activity by the anti-CEA-CAR-introduced PBMCs was observed in the CEA-positive cell strain MKN-45. Particularly, (5) CEA-zG-introduced PBMC, (9) CEA-28zG-introduced PBMC and (8) CEA-zG28-introduced PBMC exhibited strong cytotoxic activity, and it was found that a CAR having an intracellular domain of a GITR is useful in treatment of cancer.

Example 6

Re-Preparation of CEA-zG28, and Preparation of Retrovirus Solution

Since a frame shift was found in the coding region of the CD28 intracellular domain of CEA-zG28 used in Example 5, a plasmid DNA in which this frame shift was repaired was prepared, and purified using QIAGEN Plasmid Midi Kit (manufactured by Qiagen). Using this purified plasmid DNA as a DNA for transfection, a virus solution was prepared in the same manner as Example 3. The retrovirus solution thus obtained was named (8) CEA-zG28_r.

Example 7

Infection of Anti-CEA-CAR Retrovirus Vector into Human PBMC-3

Figure 8:
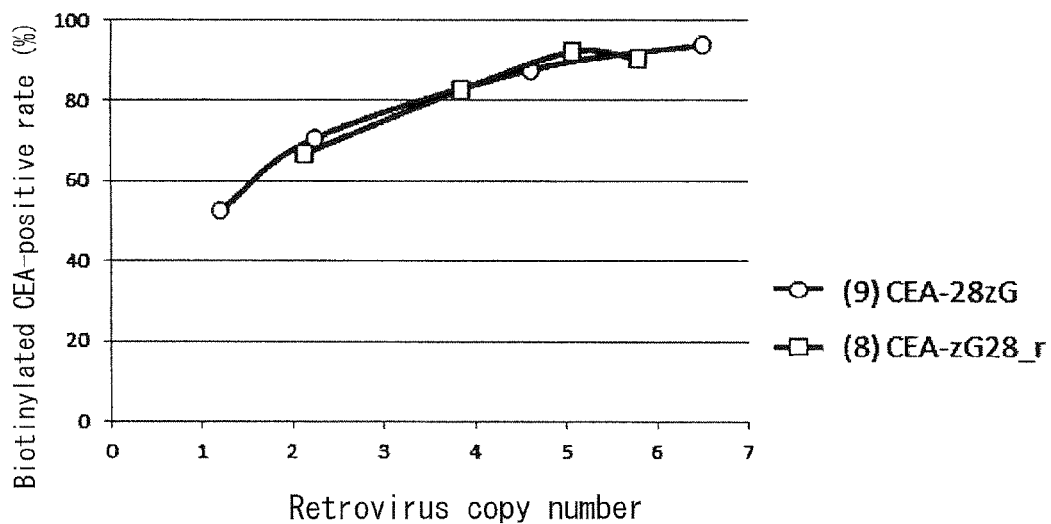
FIG. 8 shows rates of binding of CEA to CAR-introduced cells, relative to retrovirus copy numbers.
Figure 9:
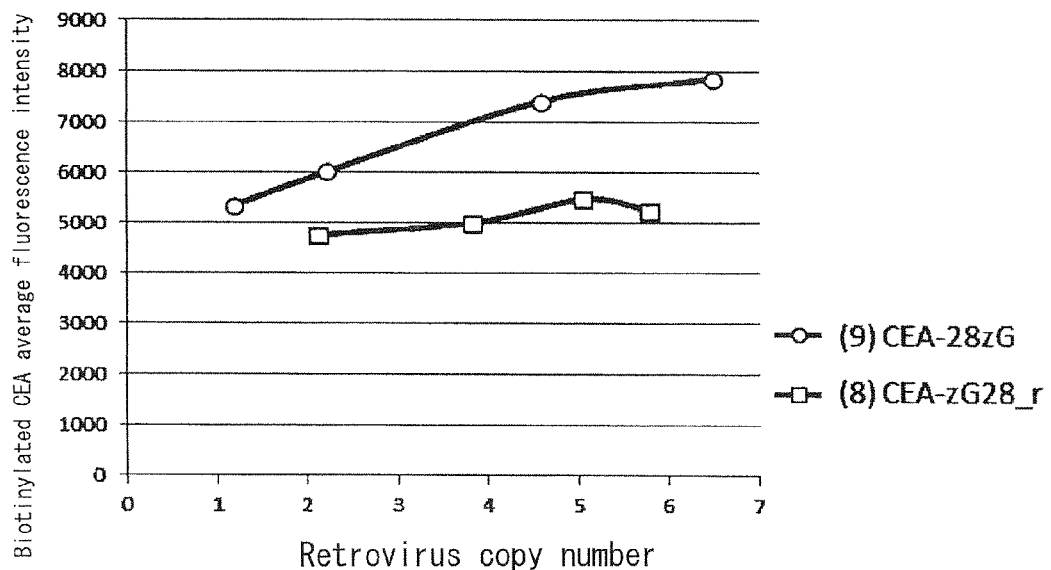
FIG. 9 shows fluorescence intensities of labeled CEA binding to CAR-introduced cells, relative to retrovirus copy numbers.

A human PBMC which had been collected after obtaining informed consent was infected with an undiluted solution or a 2-fold, 4-fold or 8-fold dilution of (8) CEA-zG28_r prepared in Example 6 or (9) CEA-28zG, and then subjected to measurement of the number of copies of the virus incorporated into the genome, a rate of cells positive for anti-CEA-CAR in CD8-positive cells, and an average fluorescence intensity of PE, in the same manner as Example 4. FIG. 8 shows the positive rates of anti-CEA-CAR relative to the copy numbers. FIG. 9 shows the PE average fluorescence intensities relative to the copy numbers. As shown in FIG. 8 and FIG. 9, it was confirmed that the cell infected with (8) CEA-zG28_r expressed anti-CEA-CAR.

Figure 10:
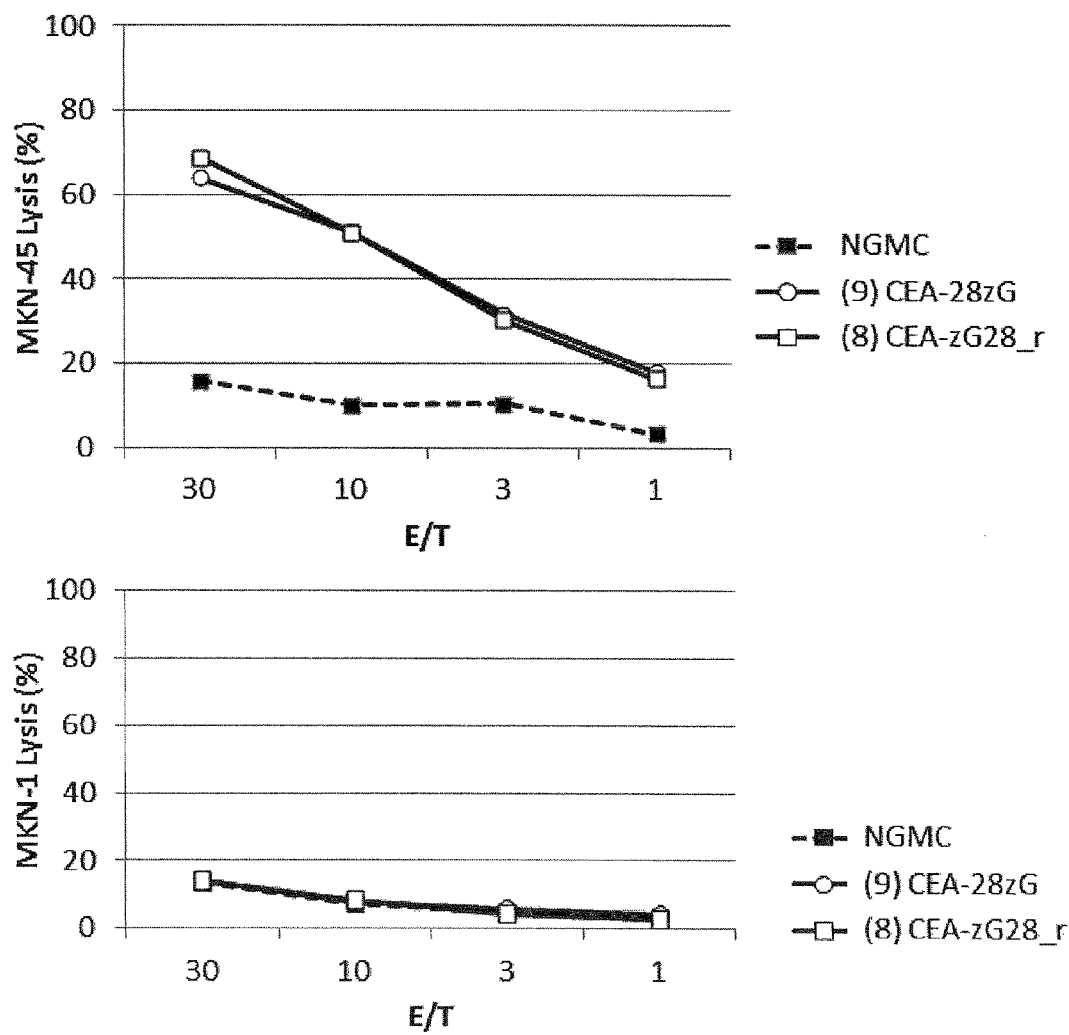
FIG. 10 shows cytotoxic activities of CAR-introduced cells.

In addition, 6 days after the second virus infection, anti-CEA-CAR-expressing cells having relatively close retrovirus copy numbers [(9) CEA-28zG: 2.22 copies, (8) CEA-zG2_r: 2.12 copies] were selected and recovered, and then subjected to measurement of cytotoxic activity against CEA-positive cell strain MKN-45 and CEA-negative cell strain MKN-1 in the same manner as Example 5. Results are shown in FIG. 10. As shown in FIG. 10, each of the anti-CEA-CAR-introduced PBMCs exhibited similar cytotoxic activity against the CEA-positive cell strain MKN-45.

Example 8

Infection of Anti-CEA-CAR Retrovirus Vector into Human PBMC-4

Figure 11:
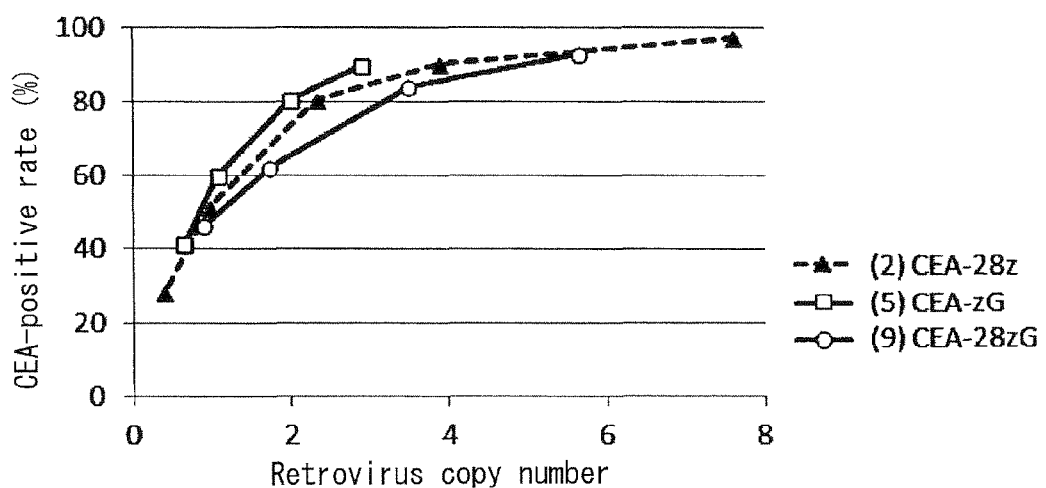
FIG. 11 shows rates of binding of CEA to CAR-introduced cells, relative to retrovirus copy numbers.
Figure 12:
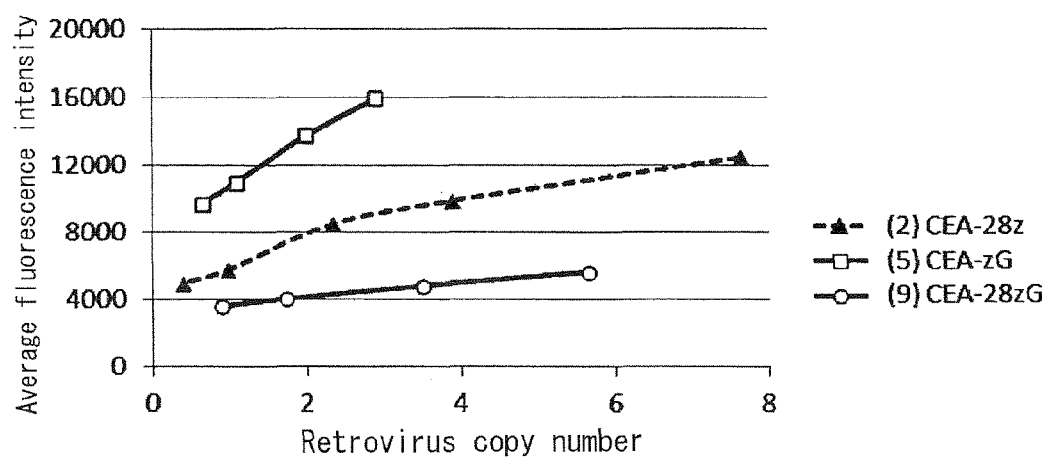
FIG. 12 shows fluorescence intensities of labeled CEA binding to CAR-introduced cells, relative to retrovirus copy numbers.

An undiluted solution and 2-fold, 4-fold and 8-fold dilutions of (5) CEA-zG and (9) CEA-28zG prepared in Example 3, and an undiluted solution and 2-fold, 4-fold, 8-fold and 16-fold dilutions of (2) CEA-28z prepared in Example 3 were prepared. A human PBMC which had been collected after obtaining informed consent was infected two times by a standard method using the above-mentioned retrovirus vector diluted solution and RetroNectin (registered trademark) to prepare a PBMC expressing each anti-CEA-CAR. Five days after the second virus infection, the infected cell was recovered, and subjected to measurement of the number of copies of the virus incorporated into the genome, a rate of cells positive for anti-CEA-CAR in CD8-positive cells, and an average fluorescence intensity of PE, in the same manner as Example 4. FIG. 11 shows the positive rates of anti-CEA-CAR relative to the copy numbers. FIG. 12 shows the PE average fluorescence intensities relative to the copy numbers. As shown in FIG. 11 and FIG. 12, the rates of cells expressing anti-CEA-CAR relative to the copy number were similar in the all cases, and (5) CEA-zG exhibited the highest average fluorescence intensity of PE relative to the copy number, that is, the highest expression amount.

In addition, 6 days after the second virus infection, the infected cell was recovered, and subjected to staining of an intracellular cytokine in a 96-well plate as described below. The anti-CEA-CAR-introduced PBMC as described above was suspended in a medium containing an intracellular transportation inhibitor, Brefeldin A (manufactured by Sigma) to $1.0 \times 10^6$ cells/mL. The suspension was added in an amount of 100 μL per well of the plate. Further, 100 μL of a $1.0 \times 10^6$ cells/mL suspension of CEA-positive cell strain MKN-45 was added to the well, and co-cultured for 5 hours. The co-cultured cells were stained with an APCcy7-labeled anti-Human CD8 antibody (manufactured by Becton Dickinson), treated with IntraPrep Reagent (manufactured by Beckman Coulter), and then stained with a PE-labeled anti-Human IFNγ antibody (manufactured by Beckman Coulter) and an APC-labeled anti-Human TNFα antibody (manufactured by eBioscience). Using a flow cytometer, the stained cells were subjected to measurement of a rate of IFNγ-producing cells in CD8-positive cells and an average fluorescence intensity of the fluorescent dye PE, and also measurement of a rate of TNFα-producing cells in CD8-positive cells and an average fluorescence intensity of the fluorescent dye APC. The average fluorescence intensities reflect the intracellular cytokine amounts of IFNγ and TNFα in an anti-CEA-CAR-positive cell.

Figure 13:
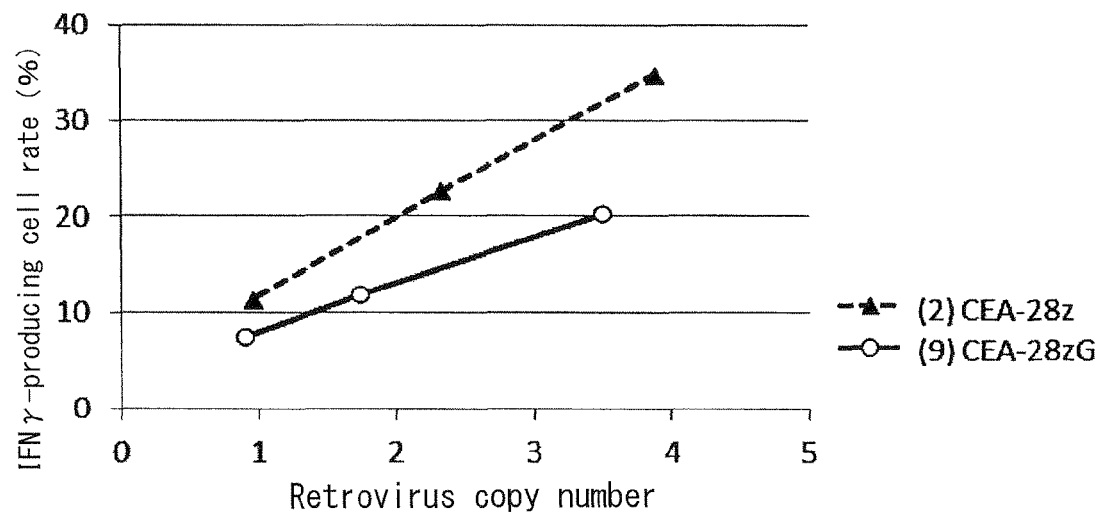
FIG. 13 shows rates of cells producing cytokine IFNγ, relative to retrovirus copy numbers.
Figure 14:
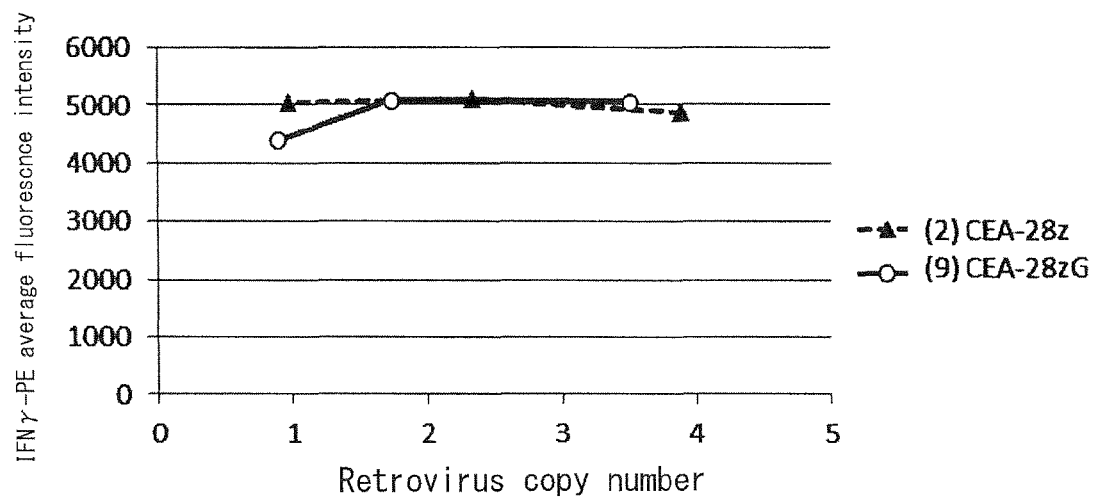
FIG. 14 shows production amounts of cytokine IFNγ, relative to retrovirus copy numbers.

FIG. 13 shows a relationship of the IFNγ-producing cell rate (ordinate axis) relative to the copy number of the retrovirus (abscissa axis). FIG. 14 shows a relationship of the PE average fluorescence intensity (ordinate axis) relative to the copy number of the retrovirus (abscissa axis). As shown in FIG. 13, (9) CEA-28zG exhibited a lower IFNγ production rate as compared with (2) CEA-28z. As shown in FIG. 14, however, it was confirmed that (9) CEA-28zG exhibited the IFNγ production amount equivalent to that of (2) CEA-28z. That is, the IFNγ production amount in an IFNγ-producing cell was higher in the (9) CEA-28zG-introduced cell.

Figure 15:
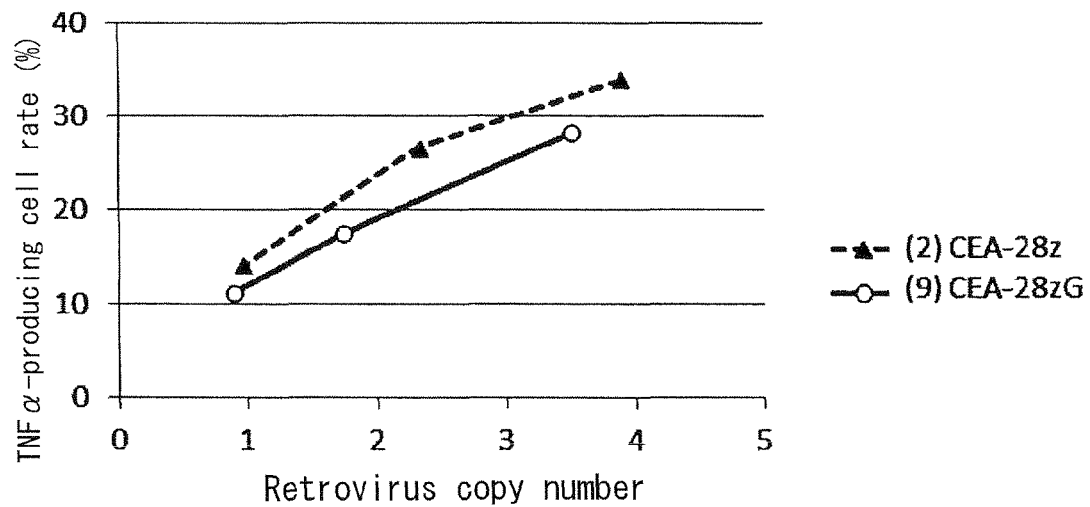
FIG. 15 shows rates of cells producing cytokine TNFα, relative to retrovirus copy numbers.
Figure 16:
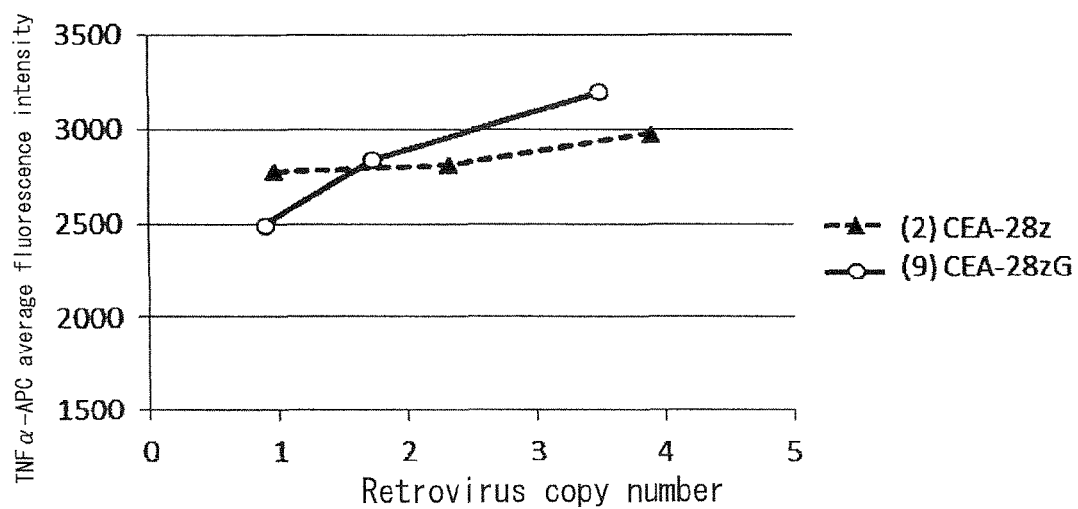
FIG. 16 shows production amounts of cytokine TNFα, relative to retrovirus copy numbers.

Similarly, FIG. 15 shows a relationship of the TNFα-producing cell rate (ordinate axis) relative to the copy number of the retrovirus (abscissa axis), and FIG. 16 shows a relationship of the APC average fluorescence intensity (ordinate axis) relative to the copy number of the retrovirus (abscissa axis). As shown in FIG. 15, (9) CEA-28zG exhibited a lower TNFα production rate than (2) CEA-28z. As shown in FIG. 16, however, (9) CEA-28zG exhibited a higher TNFα production amount. That is, similarly to the case of IFNγ, the (9) CEA-28zG-introduced cell resulted in a higher TNFα production amount in a TNFα-producing cell.

Thus, it was found that a cell having enhanced ability to produce cytokines can be produced by further loading an intracellular domain of a GITR in a CAR having an intracellular domain of CD28.

Example 9

Preparation of Anti-EGFR-CAR Expression Retrovirus Vector

An artificial synthetic gene of a base sequence shown in SEQ ID NO: 31 was prepared. This artificial synthetic gene encodes EGFR-z which is an anti-EGFR-CAR, that is, one molecule of a chimeric protein consisting of a human IgG leader sequence having an amino acid sequence shown in SEQ ID NO: 32, a scFv of an anti-EGFR monoclonal antibody which binds to a cancer antigen EGFR (Epidermal Growth Factor Receptor) having an amino acid sequence shown in SEQ ID NO: 33, a human IgG-LC (light chain constant region) domain having an amino acid sequence shown in SEQ ID NO: 34, a CD28 transmembrane domain having an amino acid sequence shown in SEQ ID NO: 24, and a CD3ζ intracellular domain having an amino acid sequence shown in SEQ ID NO: 26. A nucleic acid fragment comprising this artificial synthetic gene was cloned into a pMS3-MC vector digested with NotI-XhoI, to prepare pMS3-EGFR-LC-z-CAR expressing (1) EGFR-z having only a CD3ζ intracellular domain as the intracellular domain. The structure of the CAR corresponds to (1) in FIG. 2.

Example 10

Preparation of Anti-EGFR-CAR Expression Vector Carrying GITR Gene

Based on the pMS3-EGFR-LC-z-CAR prepared in Example 9, pMS3-EGFR-LC-28z-CAR expressing (2) EGFR-28z having an amino acid sequence shown in SEQ ID NO: 35 was prepared. Similarly, pMS3-EGFR-LC-zG-CAR expressing (5) EGFR-zG having an amino acid sequence shown in SEQ ID NO: 36, pMS3-EGFR-LC-28zG-CAR expressing (9) EGFR-28zG having an amino acid sequence shown in SEQ ID NO: 37, pMS3-EGFR-LC-z28G-CAR expressing (10) EGFR-z28G having an amino acid sequence shown in SEQ ID NO: 38, and pMS3-EGFR-LC-G28z-CAR expressing (7) EGFR-G28z having an amino acid sequence shown in SEQ ID NO: 39 were prepared. The structures of these CARs correspond to (2), (5), (9), (7) and (10) in FIG. 2, respectively.

Example 11

Preparation of Retrovirus Solution

From the plasmid vectors prepared in Examples 9 and 10, virus solutions were prepared in the same manner as Example 3. The respective viruses were named (1) EGFR-z, (2) EGFR-28z, (5) EGFR-zG, (9) EGFR-28zG, (10) EGFR-z28G, and (7) EGFR-G28z, from the structures of CARs expressed by the viruses.

Example 12

Infection of Anti-EGFR-CAR Retrovirus Vector into Human PBMC

A human PBMC which had been collected after obtaining informed consent was infected two times with an undiluted solution or a 2-fold, 4-fold or 8-fold dilution of each virus solution prepared in Example 11 by a standard method using RetroNectin (registered trademark), to prepare a PBMC expressing each anti-EGFR-CAR.

Figure 17:
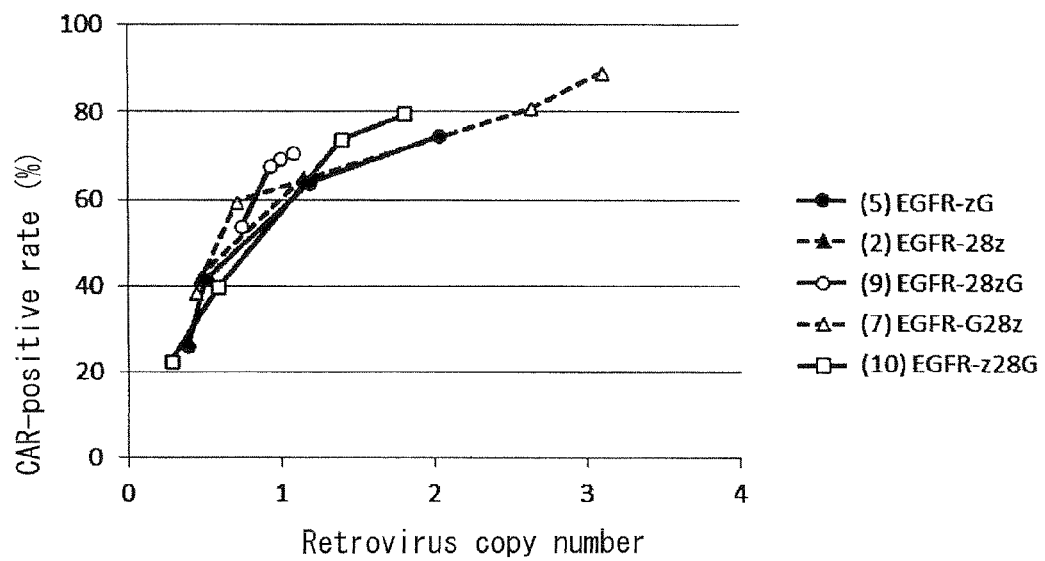
FIG. 17 shows rates of binding of EGFR (Epidermal Growth Factor Receptor) to CAR-introduced cells, relative to retrovirus copy numbers.
Figure 18:
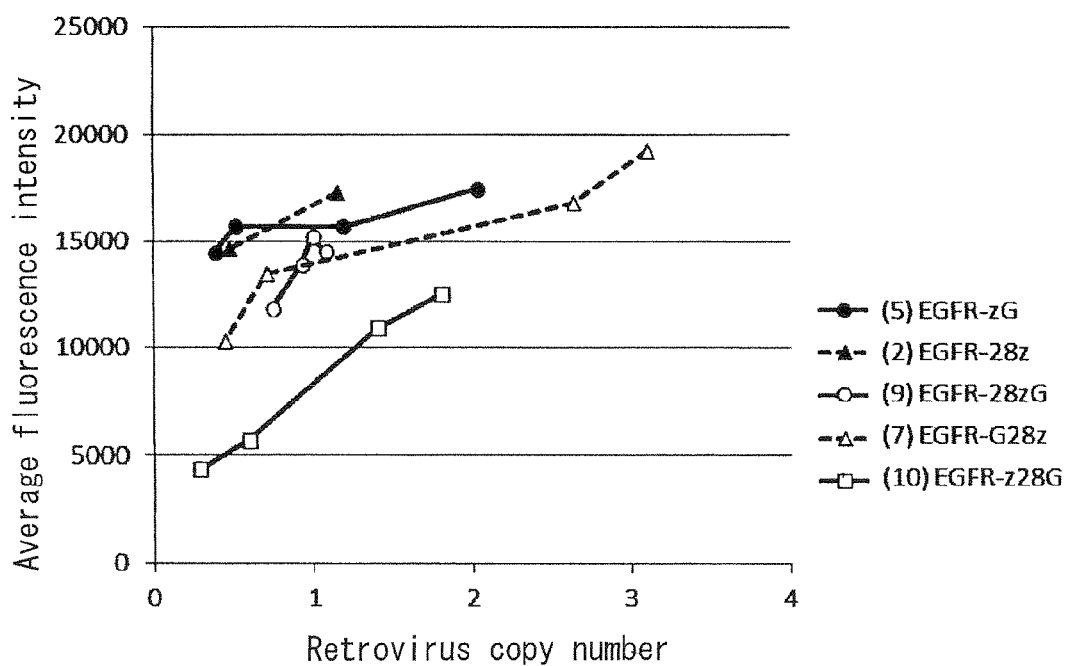
FIG. 18 shows fluorescence intensities of labeled EGFR binding to CAR-introduced cells, relative to retrovirus copy numbers.

Five days after the second virus infection, Recombinant Human EGFR (manufactured by Sino Biological) in which the C-terminal end was His-tag-modified was added to the infected cells, and then a biotin-labeled anti-His-tag antibody (manufactured by Miltenyi Biotec K.K.) was added. Thereafter, the cells were stained with streptavidin-PE (phycoerythrin: manufactured by Becton Dickinson) and a FITC-labeled anti-Human CD8 antibody (manufactured by Becton Dickinson). Using a flow cytometer, the stained cells were subjected to measurement of a rate of PE-positive cells in FITC-positive cells, that is, a rate of cells positive for CAR that binds to EGFR in CD8-positive cells. In addition, an average fluorescence intensity of the fluorescent dye PE was measured. Further, the infected cells were recovered 5 days after the second virus infection, and subjected to measurement of the number of copies of the virus incorporated into the genome in the same manner as Example 4. FIG. 17 shows the positive cell rates of anti-EGFR-CAR relative to the copy numbers of the retrovirus. FIG. 18 shows the PE average florescence intensities relative to the copy numbers of the retrovirus. As shown in FIG. 17 and FIG. 18, the expression of all anti-EGFR-CARs was confirmed.

In addition, 6 days after the second virus infection, the infected cells were recovered, and subjected to staining of an intracellular cytokine in the same manner as Example 8 except that an EGFR-positive cell strain Hela was used. In addition to IFNγ and TNFα, staining of IL-2 with FITC-labeled anti-Human IL-2 (manufactured by Becton Dickinson) was performed. Using a flow cytometer, the stained cells were subjected to measurement of a rate of cells producing each cytokine and an average fluorescence intensity of a fluorescent dye. The average fluorescence intensities reflect the intracellular cytokine amounts of IL-2, IFNγ and TNFα in an anti-CEA-CAR-positive cell.

Figure 19:
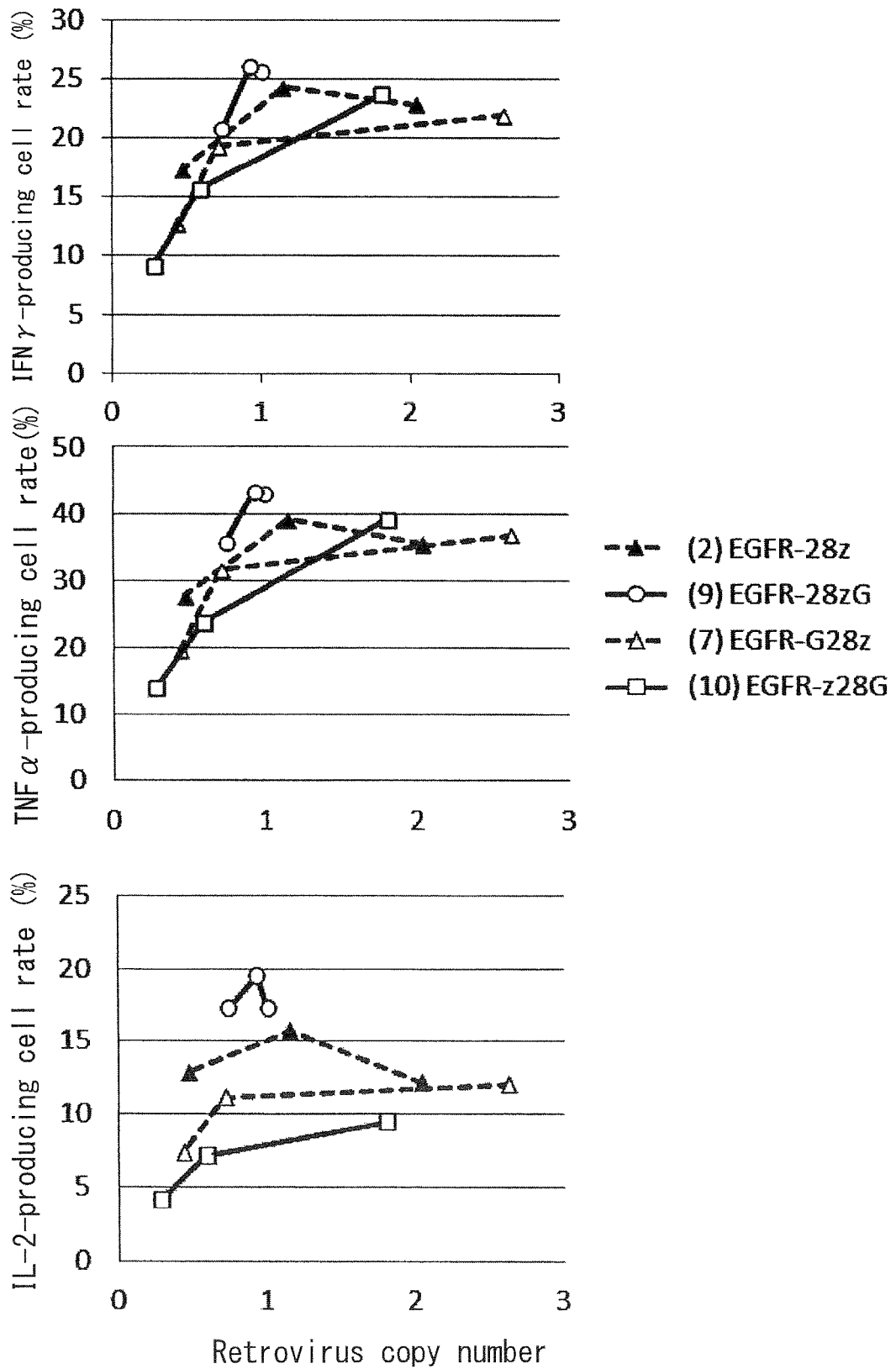
FIG. 19 shows rates of cells producing cytokines, relative to retrovirus copy numbers.
Figure 20:
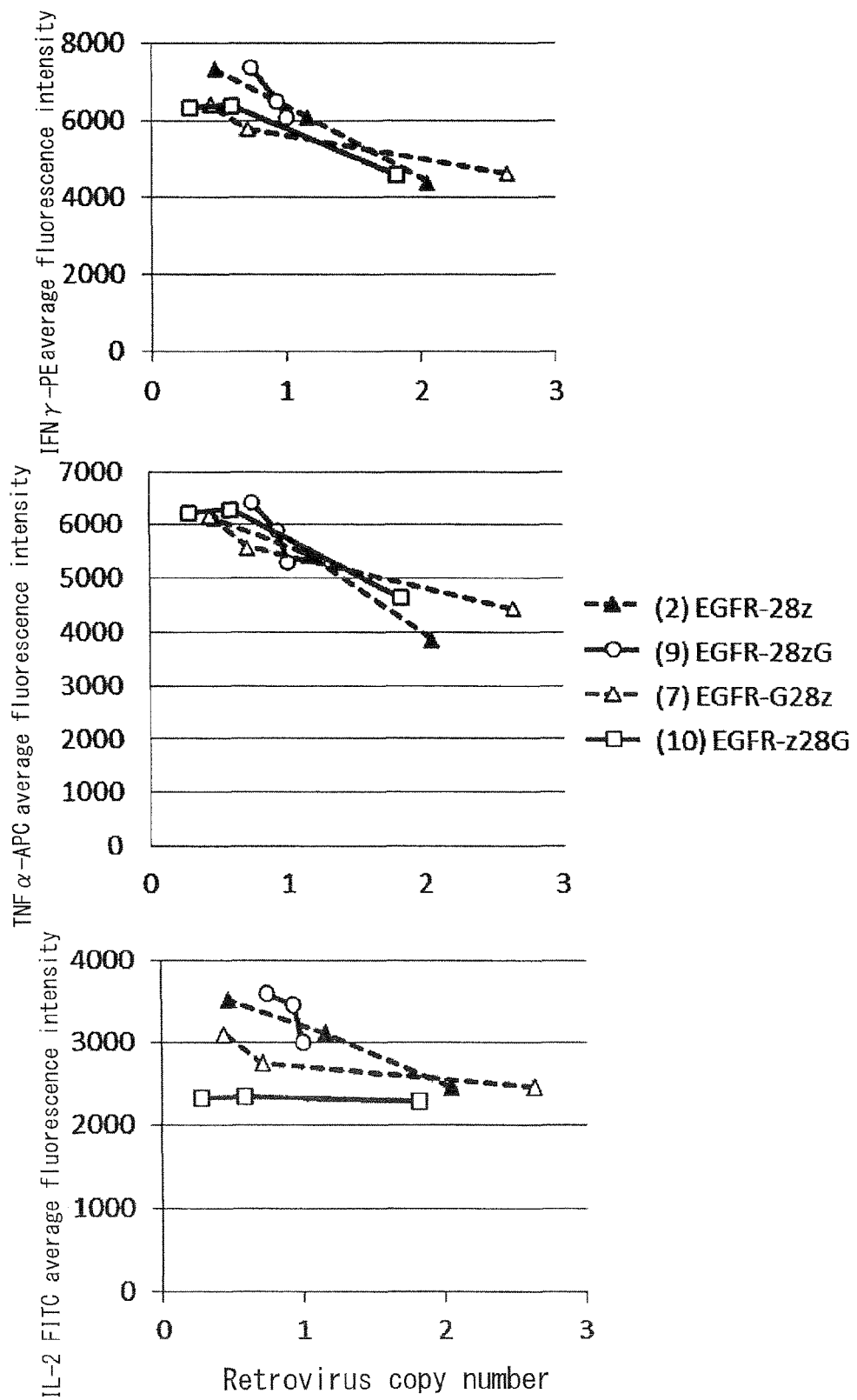
FIG. 20 shows production amounts of cytokines, relative to retrovirus copy numbers.

FIG. 19 shows a relationship of the rate of cells producing each cytokine (ordinate axis) relative to the copy number of the retrovirus (abscissa axis). FIG. 20 shows a relationship of the average fluorescence intensity (the production amount of each cytokine) (ordinate axis) relative to the copy number of the retrovirus (abscissa axis). As shown in FIG. 19 and FIG. 20, it was found that the CAR carrying an intracellular domain of a GITR tends to exhibit a higher cytokine production amount relative to the expression amount of the CAR.

INDUSTRIAL APPLICABILITY

According to the present invention, there are provided a CAR which specifically binds to a target antigen and imparts high cytotoxic activity against the target cell to a cell, a nucleic acid encoding the CAR, and a cell expressing the CAR. The CAR, nucleic acid and cell are useful in the field of adoptive immunity gene therapy targeting an antigen such as a tumor antigen.

SEQUENCE LISTING FREE TEXT

SEQ ID NO:1: 3MSCV5 primer
SEQ ID NO:2: 3MSCV3 primer
SEQ ID NO:3: Anti CEA-28z-CAR fragment sequence
SEQ ID NO:4: Anti CEA-z28-CAR fragment sequence
SEQ ID NO:5: GITR transmembrane region and cytoplasmic domain coding sequence
SEQ ID NO:6: 28TM-G-F primer
SEQ ID NO:7: G-z-R primer
SEQ ID NO:8: z-G-F primer
SEQ ID NO:9: G-MC-R primer
SEQ ID NO:10: 28SD-G-F primer
SEQ ID NO:11: hinge-G-F primer
SEQ ID NO:12: G-28SD-R primer
SEQ ID NO:13: G-28SD-R2 primer
SEQ ID NO:14: 28TM-R primer
SEQ ID NO:15: z-F primer
SEQ ID NO:16: z-R primer
SEQ ID NO:17: END-MC-F primer
SEQ ID NO:18: 28SD-R primer
SEQ ID NO:19: hinge-R primer
SEQ ID NO:20: 28SD-F primer
SEQ ID NO:21: 28SD-F2 primer
SEQ ID NO:22: Anti CEA scFv
SEQ ID NO:23: Human CD8 alpha chain hinge domain
SEQ ID NO:24: Human CD28 transmembrane domain
SEQ ID NO:25: Human CD28 cytoplasmic domain
SEQ ID NO:26: Human CD3 zeta chain cytoplasmic domain
SEQ ID NO:27: Human GITR transmembrane domain
SEQ ID NO:28: Human GITR cytoplasmic domain
SEQ ID NO:29: Anti CEA-zG-CAR sequence
SEQ ID NO:30: Anti CEA-zG28-CAR sequence
SEQ ID NO:31: Anti EGFR-LC-z-CAR coding sequence
SEQ ID NO:32: Human IgG leader sequence
SEQ ID NO:33: Anti EGFR monoclonal antibody scFv sequence
SEQ ID NO:34: Human IgG CL sequence
SEQ ID NO:35: Anti EGFR-28z-CAR sequence
SEQ ID NO:36: Anti EGFR-zG-CAR sequence
SEQ ID NO:37: Anti EGFR-28zG-CAR sequence
SEQ ID NO:38: Anti EGFR-z28G-CAR sequence
SEQ ID NO:39: Anti EGFR-G28z-CAR sequence

The invention claimed is:

1. A nucleic acid encoding a chimeric antigen receptor comprising an extracellular domain capable of binding to an antigen, a transmembrane domain, and at least one intracellular domain, wherein the intracellular domain includes an intracellular domain of a glucocorticoid-induced tumor necrosis factor receptor (GITR), the intracellular domain further includes a CD3ζ intracellular domain, and the intracellular domain of GITR is arranged on a C-terminal side relative to the CD3ζ intracellular domain, wherein a T cell or cell population comprising a T cell expressing the chimeric antigen receptor has an increased cytotoxic activity against a cell having the target antigen on the surface, as compared to a T cell or cell population comprising a T cell expressing a chimeric antigen receptor whose intracellular domain consists of an intracellular domain of CD28 and an intracellular domain of CD3ζ.

2. The nucleic acid encoding a chimeric antigen receptor according to claim 1, wherein the antigen is a tumor antigen.

3. The nucleic acid encoding a chimeric antigen receptor according to claim 1, wherein the extracellular domain capable of binding to an antigen is a single chain variable fragment of an antibody that binds to the antigen.

4. A chimeric antigen receptor comprising an extracellular domain capable of binding to an antigen, a transmembrane domain, and at least one intracellular domain, wherein the intracellular domain includes an intracellular domain of a GITR, the intracellular domain further includes a CD3ζ intracellular domain, and the intracellular domain of GITR is arranged on a C end side relative to the CD3ζ intracellular domain,
wherein a T cell or cell population comprising a T cell expressing the chimeric antigen receptor has an increased cytotoxic activity against a cell having the target antigen on the surface, as compared to a T cell or cell population comprising a T cell expressing a chimeric antigen receptor whose intracellular domain consists of an intracellular domain of CD28 and an intracellular domain of CD3ζ.

5. The chimeric antigen receptor according to claim 4, wherein the antigen is a tumor antigen.

6. The chimeric antigen receptor according to claim 4, wherein the extracellular domain capable of binding to an antigen is a single chain variable fragment of an antibody binding to the antigen.

7. A process for producing a chimeric antigen receptor-expressing cell, the process comprising a step of introducing the nucleic acid according to claim 1 into a cell, wherein the cell is a T cell or a cell population containing a T cell.

8. A chimeric antigen receptor-expressing cell in which the nucleic acid according to claim 1 is introduced, wherein the cell is a T cell or a cell population containing a T cell, and wherein the chimeric antigen receptor-expressing cell has an increased cytotoxic activity against a cell having the target antigen on the surface as compared to a cell expressing a chimeric antigen receptor whose intracellular domain consists of an intracellular domain of CD28 and an intracellular domain CD3ζ.

* * * * *

```
                             SEQUENCE LISTING

<160> NUMBER OF SEQ ID NOS: 39

<210> SEQ ID NO 1
<211> LENGTH: 34
<212> TYPE: DNA
<213> ORGANISM: Artificial
<220> FEATURE:
<223> OTHER INFORMATION: 3MSCV5 primer

<400> SEQUENCE: 1
tacctcgagc gataaaataa aagattttat ttag                              34

<210> SEQ ID NO 2
<211> LENGTH: 45
<212> TYPE: DNA
<213> ORGANISM: Artificial
<220> FEATURE:
<223> OTHER INFORMATION: 3MSCV3 primer

<400> SEQUENCE: 2
tacgaattcg attgaatccg tcgactgaaa gaccccgct gacgg                   45

<210> SEQ ID NO 3
<211> LENGTH: 1515
<212> TYPE: DNA
<213> ORGANISM: Artificial
<220> FEATURE:
<223> OTHER INFORMATION: Anti CEA-28z-CAR fragment sequence

<400> SEQUENCE: 3
atgagtgtgc ccactcaggt cctggggttg ctgctgctgt ggcttacagg tgccagatgt    60
gacatccaga tgactcagtc tccagcctcc ctttctgcat ctgtgggaga cactgtcacc   120
atcacatgtc gagcaagtga aacatttat agttatttag catggtatca gcagaaacag   180
ggaaaatctc ctcagctcct ggtctataat gcaaaggcct atcagaaggg tgtgccgtca   240
aggttcagtg gcagtggatc aggcacacag ttttctctga ggatcaacag cctgcagcct   300
gaagattttg gggattatta ctgtcaacat cattataatt ctccttatac gttcggaggg   360
```

```
gggaccaaac tggaaataaa gggttctacc tctggttctg gtaaatcttc tgaaggtaaa      420
ggtcagatcc agttggtgca gtctggacct gagctgaaga agcctggaga gacagtcaag      480
atctcctgca aggcttctgg ttattccttc acaaacgatg aataaactg  ggtgaagcag      540 gctccaggaa agggttttaa gtacatgggc tggataaaca ccatcactgg agagccaaca      600
tatactgaag acttcaaggg gcggtttgcc ttctctttgg aaacctctgc cagcactgcc      660
tatttgcaga tcaacaacct caaagatgag gacacggcta cattttctg  tgcaaagggg      720 actgggacga gcgcttactg gggccaaggg actctggtca ctgtctctgc aactagtctg      780
agcaactcca tcatgtactt cagccacttc gtgccggtct tcctgccagc gaagcccacc      840
acgacgccag cgccgcgacc accaacaccg gcgcccacca tcgcgtcgca gcccctgtcc      900
ctgcgcccag aggcgtgccg gccagcggcg ggggcgcag  tgcacacgag ggggctggac      960
tctagatttt gggtgctggt ggtggttggt ggagtcctgg cttgctatag cttgctagta     1020
acagtggcct ttattatttt ctgggtgagg agtaagagga gcaggctcct gcacagtgac     1080
tacatgaaca tgactccccg ccgccccggg cccacccgca agcattacca gccctatgcc     1140
ccaccacgcg acttcgcagc ctatcgctcc ctgagagtga agttcagcag gagcgcagac     1200 gccccccgcgt accagcaggg ccagaaccag ctctataacg agctcaatct aggacgaaga     1260
gaggagtacg atgttttgga caagagacgt ggccgggacc ctgagatggg gggaaagccg     1320
cagagaagga agaaccctca ggaaggcctg tacaatgaac tgcagaaaga taagatggcg     1380
gaggcctaca gtgagattgg gatgaaaggc gagcgccgga ggggcaaggg gcacgatggc     1440
ctttaccagg gtctcagtac agccaccaag gacacctacg acgcccttca catgcaggcc     1500
ctgccccctc gctaa                                                      1515
```

<210> SEQ ID NO 4
<211> LENGTH: 1515
<212> TYPE: DNA
<213> ORGANISM: Artificial
<220> FEATURE:
<223> OTHER INFORMATION: Anti CEA-z28-CAR fragment sequence

<400> SEQUENCE: 4

```
atgagtgtgc ccactcaggt cctggggttg ctgctgctgt ggcttacagg tgccagatgt       60
gacatccaga tgactcagtc tccagcctcc ctttctgcat ctgtgggaga cactgtcacc      120
atcacatgtc gagcaagtga gaacatttat agttatttag catggtatca gcagaaacag      180
ggaaaatctc ctcagctcct ggtctataat gcaaaggcct atcagaagg  tgtgccgtca      240 aggttcagtg gcagtggatc aggcacacag ttttctctga ggatcaacag cctgcagcct      300
gaagattttg ggattatta  ctgtcaacat cattataatt ctccttatac gttcggaggg      360
gggaccaaac tggaaataaa gggttctacc tctggttctg gtaaatcttc tgaaggtaaa      420
ggtcagatcc agttggtgca gtctggacct gagctgaaga agcctggaga gacagtcaag      480
atctcctgca aggcttctgg ttattccttc acaaacgatg aataaactg  ggtgaagcag      540 gctccaggaa agggttttaa gtacatgggc tggataaaca ccatcactgg agagccaaca      600
tatactgaag acttcaaggg gcggtttgcc ttctctttgg aaacctctgc cagcactgcc      660
tatttgcaga tcaacaacct caaagatgag gacacggcta cattttctg  tgcaaagggg      720 actgggacga gcgcttactg gggccaaggg actctggtca ctgtctctgc aactagtctg      780
agcaactcca tcatgtactt cagccacttc gtgccggtct tcctgccagc gaagcccacc      840
```

-continued

| | |
|---|---|
| acgacgccag cgccgcgacc accaacaccg gcgcccacca tcgcgtcgca gcccctgtcc | 900 |
| ctgcgcccag aggcgtgccg gccagcggcg gggggcgcag tgcacacgag ggggctggac | 960 |
| tctagatttt gggtgctggt ggtggttggt ggagtcctgg cttgctatag cttgctagta | 1020 |
| acagtggcct ttattatttt ctgggtgagg ctgagagtga agttcagcag gagcgcagac | 1080 |
| gccccgcgt accagcaggg ccagaaccag ctctataacg agctcaatct aggacgaaga | 1140 |
| gaggagtacg atgttttgga caagagacgt ggccgggacc ctgagatggg gggaaagccg | 1200 |
| cagagaagga agaaccctca ggaaggcctg tacaatgaac tgcagaaaga taagatggcg | 1260 |
| gaggcctaca gtgagattgg gatgaaaggc gagcgccgga ggggcaaggg gcacgatggc | 1320 |
| ctttaccagg gtctcagtac agccaccaag gacacctacg acgcccttca catgcaggcc | 1380 |
| ctgccccctc gcagtaagag gagcaggctc ctgcacagtg actacatgaa catgactccc | 1440 |
| cgccgccccg ggcccacccg caagcattac cagcccctatg ccccaccacg cgacttcgca | 1500 |
| gcctatcgct cctaa | 1515 |

<210> SEQ ID NO 5
<211> LENGTH: 240
<212> TYPE: DNA
<213> ORGANISM: Artificial
<220> FEATURE:
<223> OTHER INFORMATION: GITR transmembrane region and cytoplasmic
      domain coding sequence

<400> SEQUENCE: 5

| | |
|---|---|
| ccgcttgggt ggctgaccgt cgtcctcctg gccgtggccg cctgcgtcct cctcctgacc | 60 |
| tcggcccagc ttggactgca catctggcag ctgaggagtc agtgcatgtg gccccgagag | 120 |
| acccagctgc tgctggaggt gccgccgtcg accgaagacg ccagaagctg ccagttcccc | 180 |
| gaggaagagc ggggcgagcg atcggcagag agaaggggc ggctgggaga cctgtgggtg | 240 |

<210> SEQ ID NO 6
<211> LENGTH: 35
<212> TYPE: DNA
<213> ORGANISM: Artificial
<220> FEATURE:
<223> OTHER INFORMATION: 28TM-G-F primer

<400> SEQUENCE: 6

| | |
|---|---|
| attttctggg tgaggaggag tcagtgcatg tggcc | 35 |

<210> SEQ ID NO 7
<211> LENGTH: 35
<212> TYPE: DNA
<213> ORGANISM: Artificial
<220> FEATURE:
<223> OTHER INFORMATION: G-z-R primer

<400> SEQUENCE: 7

| | |
|---|---|
| gaacttcact ctcagcaccc acaggtctcc cagcc | 35 |

<210> SEQ ID NO 8
<211> LENGTH: 35
<212> TYPE: DNA
<213> ORGANISM: Artificial
<220> FEATURE:
<223> OTHER INFORMATION: z-G-F primer

<400> SEQUENCE: 8

| | |
|---|---|
| gccctgcccc ctcgcaggag tcagtgcatg tggcc | 35 |

```
<210> SEQ ID NO 9
<211> LENGTH: 35
<212> TYPE: DNA
<213> ORGANISM: Artificial
<220> FEATURE:
<223> OTHER INFORMATION: G-MC-R primer

<400> SEQUENCE: 9
ttatcgctcg agttacaccc acaggtctcc cagcc                              35

<210> SEQ ID NO 10
<211> LENGTH: 35
<212> TYPE: DNA
<213> ORGANISM: Artificial
<220> FEATURE:
<223> OTHER INFORMATION: 28SD-G-F primer

<400> SEQUENCE: 10
gcagcctatc gctccaggag tcagtgcatg tggcc                              35

<210> SEQ ID NO 11
<211> LENGTH: 35
<212> TYPE: DNA
<213> ORGANISM: Artificial
<220> FEATURE:
<223> OTHER INFORMATION: hinge-G-F primer

<400> SEQUENCE: 11 acgaggggc tggacccgct tgggtggctg accgt                               35

<210> SEQ ID NO 12
<211> LENGTH: 35
<212> TYPE: DNA
<213> ORGANISM: Artificial
<220> FEATURE:
<223> OTHER INFORMATION: G-28SD-R primer

<400> SEQUENCE: 12
actgtgcagg agcctcaccc acaggtctcc cagcc                              35

<210> SEQ ID NO 13
<211> LENGTH: 35
<212> TYPE: DNA
<213> ORGANISM: Artificial
<220> FEATURE:
<223> OTHER INFORMATION: G-28SD-R2 primer

<400> SEQUENCE: 13
cctgctcctc ttactcaccc acaggtctcc cagcc                              35

<210> SEQ ID NO 14
<211> LENGTH: 27
<212> TYPE: DNA
<213> ORGANISM: Artificial
<220> FEATURE:
<223> OTHER INFORMATION: 28TM-R primer

<400> SEQUENCE: 14
cctcacccag aaaataataa aggccac                                       27

<210> SEQ ID NO 15
<211> LENGTH: 15
<212> TYPE: DNA
<213> ORGANISM: Artificial
<220> FEATURE:
<223> OTHER INFORMATION: z-F primer
```

```
<400> SEQUENCE: 15
ctgagagtga agttc                                                         15

<210> SEQ ID NO 16
<211> LENGTH: 20
<212> TYPE: DNA
<213> ORGANISM: Artificial
<220> FEATURE:
<223> OTHER INFORMATION: z-R primer

<400> SEQUENCE: 16 gcgaggggggc agggcctgca                                                   20

<210> SEQ ID NO 17
<211> LENGTH: 20
<212> TYPE: DNA
<213> ORGANISM: Artificial
<220> FEATURE:
<223> OTHER INFORMATION: END-MC-F primer

<400> SEQUENCE: 17
taactcgagc gataaaataa                                                    20

<210> SEQ ID NO 18
<211> LENGTH: 15
<212> TYPE: DNA
<213> ORGANISM: Artificial
<220> FEATURE:
<223> OTHER INFORMATION: 28SD-R primer

<400> SEQUENCE: 18
ggagcgatag gctgc                                                         15

<210> SEQ ID NO 19
<211> LENGTH: 15
<212> TYPE: DNA
<213> ORGANISM: Artificial
<220> FEATURE:
<223> OTHER INFORMATION: hinge-R primer

<400> SEQUENCE: 19
gtccagcccc ctcgt                                                         15

<210> SEQ ID NO 20
<211> LENGTH: 15
<212> TYPE: DNA
<213> ORGANISM: Artificial
<220> FEATURE:
<223> OTHER INFORMATION: 28SD-F primer

<400> SEQUENCE: 20
agtaagagga gcagg                                                         15

<210> SEQ ID NO 21
<211> LENGTH: 20
<212> TYPE: DNA
<213> ORGANISM: Artificial
<220> FEATURE:
<223> OTHER INFORMATION: 28SD-F2 primer

<400> SEQUENCE: 21
agtaagagga gcaggctcct                                                    20

<210> SEQ ID NO 22
```

<211> LENGTH: 257
<212> TYPE: PRT
<213> ORGANISM: Artificial
<220> FEATURE:
<223> OTHER INFORMATION: Anti CEA scFv

<400> SEQUENCE: 22

```
Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Asp Thr Val Thr Ile Thr Cys Arg Ala Ser Glu Asn
        35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Ala Leu Ser Glu Gly Val Pro Ser
65                  70                  75                  80

Arg Phe Ser Gly Ser Gly Ser Gly Thr Gln Phe Ser Leu Arg Ile Asn
                85                  90                  95

Ser Leu Gln Pro Glu Asp Phe Gly Asp Tyr Tyr Cys Gln His His Tyr
            100                 105                 110

Asn Ser Pro Tyr Thr Phe Gly Gly Gly Thr Lys Leu Glu Ile Lys Gly
        115                 120                 125

Ser Thr Ser Gly Ser Gly Lys Ser Ser Glu Gly Lys Gly Gln Ile Gln
    130                 135                 140

Leu Val Gln Ser Gly Pro Glu Leu Lys Lys Pro Gly Glu Thr Val Lys
145                 150                 155                 160

Ile Ser Cys Lys Ala Ser Gly Tyr Ser Phe Thr Asn Asp Gly Ile Asn
                165                 170                 175

Trp Val Lys Gln Ala Pro Gly Lys Gly Phe Lys Tyr Met Gly Trp Ile
            180                 185                 190

Asn Thr Ile Thr Gly Glu Pro Thr Tyr Thr Glu Asp Phe Lys Gly Arg
        195                 200                 205

Phe Ala Phe Ser Leu Glu Thr Ser Ala Ser Thr Ala Tyr Leu Gln Ile
    210                 215                 220

Asn Asn Leu Lys Asp Glu Asp Thr Ala Thr Phe Phe Cys Ala Lys Gly
225                 230                 235                 240

Thr Gly Thr Ser Ala Tyr Trp Gly Gln Gly Thr Leu Val Thr Val Ser
                245                 250                 255

Ala
```

<210> SEQ ID NO 23
<211> LENGTH: 61
<212> TYPE: PRT
<213> ORGANISM: Artificial
<220> FEATURE:
<223> OTHER INFORMATION: Human CD8 alpha chain hinge domain

<400> SEQUENCE: 23

```
Leu Ser Asn Ser Ile Met Tyr Phe Ser His Phe Val Pro Val Phe Leu
1               5                   10                  15

Pro Ala Lys Pro Thr Thr Thr Pro Ala Pro Arg Pro Pro Thr Pro Ala
            20                  25                  30

Pro Thr Ile Ala Ser Gln Pro Leu Ser Leu Arg Pro Glu Ala Cys Arg
        35                  40                  45

Pro Ala Ala Gly Gly Ala Val His Thr Arg Gly Leu Asp
    50                  55                  60
```

<210> SEQ ID NO 24
<211> LENGTH: 28
<212> TYPE: PRT
<213> ORGANISM: Artificial
<220> FEATURE:
<223> OTHER INFORMATION: Human CD28 transmembrane domain

<400> SEQUENCE: 24

Phe Trp Val Leu Val Val Val Gly Gly Val Leu Ala Cys Tyr Ser Leu
1               5                   10                  15

Leu Val Thr Val Ala Phe Ile Ile Phe Trp Val Arg
            20                  25

<210> SEQ ID NO 25
<211> LENGTH: 40
<212> TYPE: PRT
<213> ORGANISM: Artificial
<220> FEATURE:
<223> OTHER INFORMATION: Human CD28 cytoplasmic domain

<400> SEQUENCE: 25

Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30

Arg Asp Phe Ala Ala Tyr Arg Ser
            35                  40

<210> SEQ ID NO 26
<211> LENGTH: 114
<212> TYPE: PRT
<213> ORGANISM: Artificial
<220> FEATURE:
<223> OTHER INFORMATION: Human CD3 zeta chain cytoplasmic domain

<400> SEQUENCE: 26

Leu Arg Val Lys Phe Ser Arg Ser Ala Asp Ala Pro Ala Tyr Gln Gln
1               5                   10                  15

Gly Gln Asn Gln Leu Tyr Asn Glu Leu Asn Leu Gly Arg Arg Glu Glu
            20                  25                  30

Tyr Asp Val Leu Asp Lys Arg Arg Gly Arg Asp Pro Glu Met Gly Gly
            35                  40                  45

Lys Pro Gln Arg Arg Lys Asn Pro Gln Glu Gly Leu Tyr Asn Glu Leu
        50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg

<210> SEQ ID NO 27
<211> LENGTH: 31
<212> TYPE: PRT
<213> ORGANISM: Artificial
<220> FEATURE:
<223> OTHER INFORMATION: Human GITR transmembrane domain

<400> SEQUENCE: 27

```
Pro Leu Gly Trp Leu Thr Val Val Leu Ala Val Ala Ala Cys Val
1               5                   10                  15
Leu Leu Leu Thr Ser Ala Gln Leu Gly Leu His Ile Trp Gln Leu
                20                  25                  30
```

<210> SEQ ID NO 28
<211> LENGTH: 49
<212> TYPE: PRT
<213> ORGANISM: Artificial
<220> FEATURE:
<223> OTHER INFORMATION: Human GITR cytoplasmic domain

<400> SEQUENCE: 28

```
Arg Ser Gln Cys Met Trp Pro Arg Glu Thr Gln Leu Leu Leu Glu Val
1               5                   10                  15
Pro Pro Ser Thr Glu Asp Ala Arg Ser Cys Gln Phe Pro Glu Glu Glu
                20                  25                  30
Arg Gly Glu Arg Ser Ala Glu Glu Lys Gly Arg Leu Gly Asp Leu Trp
        35                  40                  45
Val
```

<210> SEQ ID NO 29
<211> LENGTH: 513
<212> TYPE: PRT
<213> ORGANISM: Artificial
<220> FEATURE:
<223> OTHER INFORMATION: Anti CEA-zG-CAR sequence

<400> SEQUENCE: 29

```
Met Ser Val Pro Thr Gln Val Leu Gly Leu Leu Leu Leu Trp Leu Thr
1               5                   10                  15
Gly Ala Arg Cys Asp Ile Gln Met Thr Gln Ser Pro Ala Ser Leu Ser
                20                  25                  30
Ala Ser Val Gly Asp Thr Val Thr Ile Thr Cys Arg Ala Ser Glu Asn
        35                  40                  45
Ile Tyr Ser Tyr Leu Ala Trp Tyr Gln Gln Lys Gln Gly Lys Ser Pro
    50                  55                  60
Gln Leu Leu Val Tyr Asn Ala Lys Ala Leu Ser Glu Gly Val Pro Ser
65                  70                  75                  80
Arg Phe Ser Gly Ser Gly Ser Gly Thr Gln Phe Ser Leu Arg Ile Asn
                85                  90                  95
Ser Leu Gln Pro Glu Asp Phe Gly Asp Tyr Tyr Cys Gln His His Tyr
                100                 105                 110
Asn Ser Pro Tyr Thr Phe Gly Gly Gly Thr Lys Leu Glu Ile Lys Gly
            115                 120                 125
Ser Thr Ser Gly Ser Gly Lys Ser Ser Glu Gly Lys Gly Gln Ile Gln
        130                 135                 140
Leu Val Gln Ser Gly Pro Glu Leu Lys Lys Pro Gly Glu Thr Val Lys
145                 150                 155                 160
Ile Ser Cys Lys Ala Ser Gly Tyr Ser Phe Thr Asn Asp Gly Ile Asn
                165                 170                 175
Trp Val Lys Gln Ala Pro Gly Lys Gly Phe Lys Tyr Met Gly Trp Ile
            180                 185                 190
Asn Thr Ile Thr Gly Glu Pro Thr Tyr Thr Glu Asp Phe Lys Gly Arg
        195                 200                 205
Phe Ala Phe Ser Leu Glu Thr Ser Ala Ser Thr Ala Tyr Leu Gln Ile
    210                 215                 220
```

```
Asn Asn Leu Lys Asp Glu Asp Thr Ala Thr Phe Phe Cys Ala Lys Gly
225                 230                 235                 240

Thr Gly Thr Ser Ala Tyr Trp Gly Gln Gly Thr Leu Val Thr Val Ser
            245                 250                 255

Ala Thr Ser Leu Ser Asn Ser Ile Met Tyr Phe Ser His Phe Val Pro
        260                 265                 270

Val Phe Leu Pro Ala Lys Pro Thr Thr Thr Pro Ala Pro Arg Pro Pro
    275                 280                 285

Thr Pro Ala Pro Thr Ile Ala Ser Gln Pro Leu Ser Leu Arg Pro Glu
290                 295                 300

Ala Cys Arg Pro Ala Ala Gly Gly Ala Val His Thr Arg Gly Leu Asp
305                 310                 315                 320

Ser Arg Phe Trp Val Leu Val Val Val Gly Gly Val Leu Ala Cys Tyr
            325                 330                 335

Ser Leu Leu Val Thr Val Ala Phe Ile Ile Phe Trp Val Arg Leu Arg
        340                 345                 350

Val Lys Phe Ser Arg Ser Ala Asp Ala Pro Ala Tyr Gln Gln Gly Gln
    355                 360                 365

Asn Gln Leu Tyr Asn Glu Leu Asn Leu Gly Arg Arg Glu Glu Tyr Asp
370                 375                 380

Val Leu Asp Lys Arg Arg Gly Arg Asp Pro Glu Met Gly Gly Lys Pro
385                 390                 395                 400

Gln Arg Arg Lys Asn Pro Gln Glu Gly Leu Tyr Asn Glu Leu Gln Lys
            405                 410                 415

Asp Lys Met Ala Glu Ala Tyr Ser Glu Ile Gly Met Lys Gly Glu Arg
        420                 425                 430

Arg Arg Gly Lys Gly His Asp Gly Leu Tyr Gln Gly Leu Ser Thr Ala
    435                 440                 445

Thr Lys Asp Thr Tyr Asp Ala Leu His Met Gln Ala Leu Pro Pro Arg
450                 455                 460

Arg Ser Gln Cys Met Trp Pro Arg Glu Thr Gln Leu Leu Leu Glu Val
465                 470                 475                 480

Pro Pro Ser Thr Glu Asp Ala Arg Ser Cys Gln Phe Pro Glu Glu Glu
            485                 490                 495

Arg Gly Glu Arg Ser Ala Glu Glu Lys Gly Arg Leu Gly Asp Leu Trp
        500                 505                 510

Val

<210> SEQ ID NO 30
<211> LENGTH: 553
<212> TYPE: PRT
<213> ORGANISM: Artificial
<220> FEATURE:
<223> OTHER INFORMATION: Anti CEA-zG28-CAR sequence

<400> SEQUENCE: 30

Met Ser Val Pro Thr Gln Val Leu Gly Leu Leu Leu Leu Trp Leu Thr
1               5                   10                  15

Gly Ala Arg Cys Asp Ile Gln Met Thr Gln Ser Pro Ala Ser Leu Ser
            20                  25                  30

Ala Ser Val Gly Asp Thr Val Thr Ile Thr Cys Arg Ala Ser Glu Asn
        35                  40                  45

Ile Tyr Ser Tyr Leu Ala Trp Tyr Gln Gln Lys Gln Gly Lys Ser Pro
    50                  55                  60

Gln Leu Leu Val Tyr Asn Ala Lys Ala Leu Ser Glu Gly Val Pro Ser
```

```
                65                  70                  75                  80
        Arg Phe Ser Gly Ser Gly Ser Gly Thr Gln Phe Ser Leu Arg Ile Asn
                        85                  90                  95

Ser Leu Gln Pro Glu Asp Phe Gly Asp Tyr Tyr Cys Gln His His Tyr
                       100                 105                 110

Asn Ser Pro Tyr Thr Phe Gly Gly Thr Lys Leu Glu Ile Lys Gly
                       115                 120                 125

Ser Thr Ser Gly Ser Gly Lys Ser Ser Glu Gly Lys Gly Gln Ile Gln
                       130                 135                 140

Leu Val Gln Ser Gly Pro Glu Leu Lys Lys Pro Gly Glu Thr Val Lys
        145                 150                 155                 160

Ile Ser Cys Lys Ala Ser Gly Tyr Ser Phe Thr Asn Asp Gly Ile Asn
                            165                 170                 175

Trp Val Lys Gln Ala Pro Gly Lys Gly Phe Lys Tyr Met Gly Trp Ile
                       180                 185                 190

Asn Thr Ile Thr Gly Glu Pro Thr Tyr Thr Glu Asp Phe Lys Gly Arg
                       195                 200                 205

Phe Ala Phe Ser Leu Glu Thr Ser Ala Ser Thr Ala Tyr Leu Gln Ile
                       210                 215                 220

Asn Asn Leu Lys Asp Glu Asp Thr Ala Thr Phe Phe Cys Ala Lys Gly
        225                 230                 235                 240

Thr Gly Thr Ser Ala Tyr Trp Gly Gln Gly Thr Leu Val Thr Val Ser
                            245                 250                 255

Ala Thr Ser Leu Ser Asn Ser Ile Met Tyr Phe Ser His Phe Val Pro
                       260                 265                 270

Val Phe Leu Pro Ala Lys Pro Thr Thr Thr Pro Ala Pro Arg Pro Pro
                       275                 280                 285

Thr Pro Ala Pro Thr Ile Ala Ser Gln Pro Leu Ser Leu Arg Pro Glu
                       290                 295                 300

Ala Cys Arg Pro Ala Ala Gly Gly Ala Val His Thr Arg Gly Leu Asp
        305                 310                 315                 320

Ser Arg Phe Trp Val Leu Val Val Val Gly Gly Val Leu Ala Cys Tyr
                            325                 330                 335

Ser Leu Leu Val Thr Val Ala Phe Ile Ile Phe Trp Val Arg Leu Arg
                       340                 345                 350

Val Lys Phe Ser Arg Ser Ala Asp Ala Pro Ala Tyr Gln Gln Gly Gln
                       355                 360                 365

Asn Gln Leu Tyr Asn Glu Leu Asn Leu Gly Arg Arg Glu Glu Tyr Asp
                       370                 375                 380

Val Leu Asp Lys Arg Arg Gly Arg Asp Pro Glu Met Gly Gly Lys Pro
        385                 390                 395                 400

Gln Arg Arg Lys Asn Pro Gln Glu Gly Leu Tyr Asn Glu Leu Gln Lys
                            405                 410                 415

Asp Lys Met Ala Glu Ala Tyr Ser Glu Ile Gly Met Lys Gly Glu Arg
                       420                 425                 430

Arg Arg Gly Lys Gly His Asp Gly Leu Tyr Gln Gly Leu Ser Thr Ala
                       435                 440                 445

Thr Lys Asp Thr Tyr Asp Ala Leu His Met Gln Ala Leu Pro Pro Arg
                       450                 455                 460

Arg Ser Gln Cys Met Trp Pro Arg Glu Thr Gln Leu Leu Leu Glu Val
        465                 470                 475                 480

Pro Pro Ser Thr Glu Asp Ala Arg Ser Cys Gln Phe Pro Glu Glu Glu
                            485                 490                 495
```

Arg Gly Glu Arg Ser Ala Glu Glu Lys Gly Arg Leu Gly Asp Leu Trp
            500                 505                 510

Val Ser Lys Arg Ser Arg Leu Leu His Ser Asp Tyr Met Asn Met Thr
            515                 520                 525

Pro Arg Arg Pro Gly Pro Thr Arg Lys His Tyr Gln Pro Tyr Ala Pro
            530                 535                 540

Pro Arg Asp Phe Ala Ala Tyr Arg Ser
545                 550

<210> SEQ ID NO 31
<211> LENGTH: 1545
<212> TYPE: DNA
<213> ORGANISM: Artificial Sequence
<220> FEATURE:
<223> OTHER INFORMATION: Anti EGFR-LC-z-CAR coding sequence

<400> SEQUENCE: 31

| | | | |
|---|---|---|---|
| atgaaacacc tgtggttctt cctcctgctg gtggcagctc ccagatgggt cctgtcccag | | | 60 |
| gtgcagctgc aggagtcggg cccaggactg gtgaagcctt cggagaccct gtccctcacc | | | 120 |
| tgcactgtct ctggtggctc catcagcagt agtagttact actggggctg gatccgccag | | | 180 |
| cccccaggga aggggctgga gtggattggg agtatctatt atagtgggag cacctactac | | | 240 |
| aacccgtccc tcaagagtcg agtcaccata tccgtagaca cgtccaagaa ccagttctcc | | | 300 |
| ctgaagctga gctctgtgac cgccgcagac acggctgtgt attactgtgc gagacttcct | | | 360 |
| atggttacga tgtcctttga ctactggggc cagggaaccc tggtcaccgt ctcgagaggc | | | 420 |
| ggtggcggat caggtggcgg tggaagtggc ggtggtgggt ccatggcctc ctatgtgctg | | | 480 |
| actcagccac cctcagtgtc agtggcccca ggaaagacgg ccaggattac ctgtggggga | | | 540 |
| aacaacattg gaagtaaaag tgtgcactgg taccagcaga agccaggcca ggcccctgtg | | | 600 |
| ctggtcatct attatgatag cgaccggccc tcagggatcc ctgagcgatt ctctggctcc | | | 660 |
| aactctggga acacggccac cctgaccatc agcagggtcg aagccgggga tgaggccgac | | | 720 |
| tattactgtc aggtgtggga tagtagtagt gatcatgtgg tattcggcgg agggaccaag | | | 780 |
| ctgaccgtcc taggtcagcc caaggctgcc ccctcggtca ctctgttccc gccctcctct | | | 840 |
| gaggagcttc aagccaacaa ggccacactg gtgtgtctca taagtgactt ctacccggga | | | 900 |
| gccgtgacag tggcttggaa ggcagatagc agccccgtca aggcgggagt ggagaccacc | | | 960 |
| acaccctcca acaaagcaa caacaagtac gcggccagca gctatctgag cctgacgcct | | | 1020 |
| gagcagtgga agtcccacag aagctacagc tgccaggtca cgcatgaagg gagcaccgtg | | | 1080 |
| gagaagacag tggcccctac agaatgttcg actagatttt gggtgctggt ggtggttggt | | | 1140 |
| ggagtcctgg cttgctatag cttgctagta acagtggcct ttattatttt ctgggtgagg | | | 1200 |
| ctgagagtga agttcagcag gagcgcagac gccccgcgt accagcaggg ccagaaccag | | | 1260 |
| ctctataacg agctcaatct aggacgaaga gaggagtacg atgttttgga caagagacgt | | | 1320 |
| ggccgggacc ctgagatggg gggaaagccg cagagaagga gaaccctca ggaaggcctg | | | 1380 |
| tacaatgaac tgcagaaaga taagatggcg gaggcctaca gtgagattgg gatgaaaggc | | | 1440 |
| gagcgccgga ggggcaaggg gcacgatggc ctttaccagg gtctcagtac agccaccaag | | | 1500 |
| gacacctacg acgcccttca catgcaggcc ctgccccctc gctaa | | | 1545 |

<210> SEQ ID NO 32
<211> LENGTH: 19
<212> TYPE: PRT

<213> ORGANISM: Artificial Sequence
<220> FEATURE:
<223> OTHER INFORMATION: Human IgG leader sequence

<400> SEQUENCE: 32

Met Lys His Leu Trp Phe Phe Leu Leu Leu Val Ala Ala Pro Arg Trp
1               5                   10                  15

Val Leu Ser

<210> SEQ ID NO 33
<211> LENGTH: 245
<212> TYPE: PRT
<213> ORGANISM: Artificial Sequence
<220> FEATURE:
<223> OTHER INFORMATION: Anti EGFR monoclonal antibody scFv sequence

<400> SEQUENCE: 33

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Leu Pro Met Val Thr Met Ser Phe Asp Tyr Trp Gly Gln
            100                 105                 110

Gly Thr Leu Val Thr Val Ser Arg Gly Gly Gly Gly Ser Gly Gly Gly
        115                 120                 125

Gly Ser Gly Gly Gly Gly Ser Met Ala Ser Tyr Val Leu Thr Gln Pro
130                 135                 140

Pro Ser Val Ser Val Ala Pro Gly Lys Thr Ala Arg Ile Thr Cys Gly
145                 150                 155                 160

Gly Asn Asn Ile Gly Ser Lys Ser Val His Trp Tyr Gln Gln Lys Pro
                165                 170                 175

Gly Gln Ala Pro Val Leu Val Ile Tyr Tyr Asp Ser Asp Arg Pro Ser
            180                 185                 190

Gly Ile Pro Glu Arg Phe Ser Gly Ser Asn Ser Gly Asn Thr Ala Thr
        195                 200                 205

Leu Thr Ile Ser Arg Val Glu Ala Gly Asp Glu Ala Asp Tyr Tyr Cys
210                 215                 220

Gln Val Trp Asp Ser Ser Ser Asp His Val Val Phe Gly Gly Gly Thr
225                 230                 235                 240

Lys Leu Thr Val Leu
            245

<210> SEQ ID NO 34
<211> LENGTH: 106
<212> TYPE: PRT
<213> ORGANISM: Artificial Sequence
<220> FEATURE:
<223> OTHER INFORMATION: Human IgG CL sequence

<400> SEQUENCE: 34

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 35
<211> LENGTH: 554
<212> TYPE: PRT
<213> ORGANISM: Artificial Sequence
<220> FEATURE:
<223> OTHER INFORMATION: Anti EGFR-28z-CAR sequence

<400> SEQUENCE: 35

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Ser Ser Tyr Tyr Trp Gly Trp Ile Arg Gln Pro Pro Gly Lys
50                  55                  60

Gly Leu Glu Trp Ile Gly Ser Ile Tyr Tyr Ser Gly Ser Thr Tyr Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Leu Pro Met Val Thr Met Ser Phe Asp Tyr
        115                 120                 125

Trp Gly Gln Gly Thr Leu Val Thr Val Ser Arg Gly Gly Gly Gly Ser
130                 135                 140

Gly Gly Gly Gly Ser Gly Gly Gly Ser Met Ala Ser Tyr Val Leu
145                 150                 155                 160

Thr Gln Pro Pro Ser Val Ser Val Ala Pro Gly Lys Thr Ala Arg Ile
                165                 170                 175

Thr Cys Gly Gly Asn Asn Ile Gly Ser Lys Ser Val His Trp Tyr Gln
            180                 185                 190

Gln Lys Pro Gly Gln Ala Pro Val Leu Val Ile Tyr Tyr Asp Ser Asp
        195                 200                 205

Arg Pro Ser Gly Ile Pro Glu Arg Phe Ser Gly Ser Asn Ser Gly Asn
210                 215                 220

Thr Ala Thr Leu Thr Ile Ser Arg Val Glu Ala Gly Asp Glu Ala Asp
225                 230                 235                 240

Tyr Tyr Cys Gln Val Trp Asp Ser Ser Ser Asp His Val Val Phe Gly
                245                 250                 255

Gly Gly Thr Lys Leu Thr Val Leu Gly Gln Pro Lys Ala Ala Pro Ser
                260                 265                 270

Val Thr Leu Phe Pro Pro Ser Ser Glu Glu Leu Gln Ala Asn Lys Ala
            275                 280                 285

Thr Leu Val Cys Leu Ile Ser Asp Phe Tyr Pro Gly Ala Val Thr Val
        290                 295                 300

Ala Trp Lys Ala Asp Ser Ser Pro Val Lys Ala Gly Val Glu Thr Thr
305                 310                 315                 320

Thr Pro Ser Lys Gln Ser Asn Asn Lys Tyr Ala Ala Ser Ser Tyr Leu
                325                 330                 335

Ser Leu Thr Pro Glu Gln Trp Lys Ser His Arg Ser Tyr Ser Cys Gln
            340                 345                 350

Val Thr His Glu Gly Ser Thr Val Glu Lys Thr Val Ala Pro Thr Glu
        355                 360                 365

Cys Ser Thr Arg Phe Trp Val Leu Val Val Val Gly Gly Val Leu Ala
370                 375                 380

Cys Tyr Ser Leu Leu Val Thr Val Ala Phe Ile Ile Phe Trp Val Arg
385                 390                 395                 400

Ser Lys Arg Ser Arg Leu Leu His Ser Asp Tyr Met Asn Met Thr Pro
                405                 410                 415

Arg Arg Pro Gly Pro Thr Arg Lys His Tyr Gln Pro Tyr Ala Pro Pro
            420                 425                 430

Arg Asp Phe Ala Ala Tyr Arg Ser Leu Arg Val Lys Phe Ser Arg Ser
        435                 440                 445

Ala Asp Ala Pro Ala Tyr Gln Gln Gly Gln Asn Gln Leu Tyr Asn Glu
450                 455                 460

Leu Asn Leu Gly Arg Arg Glu Glu Tyr Asp Val Leu Asp Lys Arg Arg
465                 470                 475                 480

Gly Arg Asp Pro Glu Met Gly Gly Lys Pro Gln Arg Arg Lys Asn Pro
                485                 490                 495

Gln Glu Gly Leu Tyr Asn Glu Leu Gln Lys Asp Lys Met Ala Glu Ala
            500                 505                 510

Tyr Ser Glu Ile Gly Met Lys Gly Glu Arg Arg Arg Gly Lys Gly His
        515                 520                 525

Asp Gly Leu Tyr Gln Gly Leu Ser Thr Ala Thr Lys Asp Thr Tyr Asp
530                 535                 540

Ala Leu His Met Gln Ala Leu Pro Pro Arg
545                 550

<210> SEQ ID NO 36
<211> LENGTH: 563
<212> TYPE: PRT
<213> ORGANISM: Artificial Sequence
<220> FEATURE:
<223> OTHER INFORMATION: Anti EGFR-zG-CAR sequence

<400> SEQUENCE: 36

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Ser Ser Tyr Tyr Trp Gly Trp Ile Arg Gln Pro Pro Gly Lys
    50                  55                  60

```
Gly Leu Glu Trp Ile Gly Ser Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Ser Val Thr Ala Ala Asp Thr Ala
            100                 105                 110

Val Tyr Tyr Cys Ala Arg Leu Pro Met Val Thr Met Ser Phe Asp Tyr
        115                 120                 125

Trp Gly Gln Gly Thr Leu Thr Val Ser Arg Gly Gly Gly Gly Ser
    130                 135                 140

Gly Gly Gly Gly Ser Gly Gly Gly Ser Met Ala Ser Tyr Val Leu
145                 150                 155                 160

Thr Gln Pro Pro Ser Val Ser Val Ala Pro Gly Lys Thr Ala Arg Ile
                165                 170                 175

Thr Cys Gly Gly Asn Asn Ile Gly Ser Lys Ser Val His Trp Tyr Gln
            180                 185                 190

Gln Lys Pro Gly Gln Ala Pro Val Leu Val Ile Tyr Tyr Asp Ser Asp
        195                 200                 205

Arg Pro Ser Gly Ile Pro Glu Arg Phe Ser Gly Ser Asn Ser Gly Asn
210                 215                 220

Thr Ala Thr Leu Thr Ile Ser Arg Val Glu Ala Gly Asp Glu Ala Asp
225                 230                 235                 240

Tyr Tyr Cys Gln Val Trp Asp Ser Ser Asp His Val Val Phe Gly
                245                 250                 255

Gly Gly Thr Lys Leu Thr Val Leu Gly Gln Pro Lys Ala Ala Pro Ser
            260                 265                 270

Val Thr Leu Phe Pro Pro Ser Ser Glu Glu Leu Gln Ala Asn Lys Ala
        275                 280                 285

Thr Leu Val Cys Leu Ile Ser Asp Phe Tyr Pro Gly Ala Val Thr Val
    290                 295                 300

Ala Trp Lys Ala Asp Ser Ser Pro Val Lys Ala Gly Val Glu Thr Thr
305                 310                 315                 320

Thr Pro Ser Lys Gln Ser Asn Asn Lys Tyr Ala Ala Ser Ser Tyr Leu
                325                 330                 335

Ser Leu Thr Pro Glu Gln Trp Lys Ser His Arg Ser Tyr Ser Cys Gln
            340                 345                 350

Val Thr His Glu Gly Ser Thr Val Glu Lys Thr Val Ala Pro Thr Glu
        355                 360                 365

Cys Ser Thr Arg Phe Trp Val Leu Val Val Val Gly Gly Val Leu Ala
370                 375                 380

Cys Tyr Ser Leu Leu Val Thr Val Ala Phe Ile Ile Phe Trp Val Arg
385                 390                 395                 400

Leu Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
            420                 425                 430

Tyr Asp Val Leu Asp Lys Arg Arg Gly Arg Asp Pro Glu Met Gly Gly
        435                 440                 445

Lys Pro Gln Arg Arg Lys Asn Pro Gln Glu Gly Leu Tyr Asn Glu Leu
    450                 455                 460

Gln Lys Asp Lys Met Ala Glu Ala Tyr Ser Glu Ile Gly Met Lys Gly
465                 470                 475                 480

Glu Arg Arg Arg Gly Lys Gly His Asp Gly Leu Tyr Gln Gly Leu Ser
```

```
                485                 490                 495
Thr Ala Thr Lys Asp Thr Tyr Asp Ala Leu His Met Gln Ala Leu Pro
            500                 505                 510
Pro Arg Arg Ser Gln Cys Met Trp Pro Arg Glu Thr Gln Leu Leu Leu
            515                 520                 525
Glu Val Pro Pro Ser Thr Glu Asp Ala Arg Ser Cys Gln Phe Pro Glu
530             535                 540
Glu Glu Arg Gly Glu Arg Ser Ala Glu Lys Gly Arg Leu Gly Asp
545             550                 555                 560
Leu Trp Val

<210> SEQ ID NO 37
<211> LENGTH: 603
<212> TYPE: PRT
<213> ORGANISM: Artificial Sequence
<220> FEATURE:
<223> OTHER INFORMATION: Anti EGFR-28zG-CAR sequence

<400> SEQUENCE: 37

Met Lys His Leu Trp Phe Phe Leu Leu Leu Val Ala Ala Pro Arg Trp
1               5                   10                  15
Val Leu Ser Gln Val Gln Leu Gln Glu Ser Gly Pro Gly Leu Val Lys
            20                  25                  30
Pro Ser Glu Thr Leu Ser Leu Thr Cys Thr Val Ser Gly Gly Ser Ile
        35                  40                  45
Ser Ser Ser Ser Tyr Tyr Trp Gly Trp Ile Arg Gln Pro Pro Gly Lys
    50                  55                  60
Gly Leu Glu Trp Ile Gly Ser Ile Tyr Tyr Ser Gly Ser Thr Tyr Tyr
65                  70                  75                  80
Asn Pro Ser Leu Lys Ser Arg Val Thr Ile Ser Val Asp Thr Ser Lys
                85                  90                  95
Asn Gln Phe Ser Leu Lys Leu Ser Ser Val Thr Ala Ala Asp Thr Ala
            100                 105                 110
Val Tyr Tyr Cys Ala Arg Leu Pro Met Val Thr Met Ser Phe Asp Tyr
        115                 120                 125
Trp Gly Gln Gly Thr Leu Val Thr Val Ser Arg Gly Gly Gly Gly Ser
    130                 135                 140
Gly Gly Gly Gly Ser Gly Gly Gly Ser Met Ala Ser Tyr Val Leu
145                 150                 155                 160
Thr Gln Pro Pro Ser Val Ser Val Ala Pro Gly Lys Thr Ala Arg Ile
                165                 170                 175
Thr Cys Gly Gly Asn Asn Ile Gly Ser Lys Ser Val His Trp Tyr Gln
            180                 185                 190
Gln Lys Pro Gly Gln Ala Pro Val Leu Val Ile Tyr Tyr Asp Ser Asp
        195                 200                 205
Arg Pro Ser Gly Ile Pro Glu Arg Phe Ser Gly Ser Asn Ser Gly Asn
    210                 215                 220
Thr Ala Thr Leu Thr Ile Ser Arg Val Glu Ala Gly Asp Glu Ala Asp
225                 230                 235                 240
Tyr Tyr Cys Gln Val Trp Asp Ser Ser Asp His Val Val Phe Gly
                245                 250                 255
Gly Gly Thr Lys Leu Thr Val Leu Gly Gln Pro Lys Ala Ala Pro Ser
            260                 265                 270
Val Thr Leu Phe Pro Pro Ser Ser Glu Glu Leu Gln Ala Asn Lys Ala
        275                 280                 285
```

```
Thr Leu Val Cys Leu Ile Ser Asp Phe Tyr Pro Gly Ala Thr Val
    290                 295                 300

Ala Trp Lys Ala Asp Ser Ser Pro Val Lys Ala Gly Val Glu Thr Thr
305                 310                 315                 320

Thr Pro Ser Lys Gln Ser Asn Asn Lys Tyr Ala Ala Ser Ser Tyr Leu
                325                 330                 335

Ser Leu Thr Pro Glu Gln Trp Lys Ser His Arg Ser Tyr Ser Cys Gln
                340                 345                 350

Val Thr His Glu Gly Ser Thr Val Glu Lys Thr Val Ala Pro Thr Glu
                355                 360                 365

Cys Ser Thr Arg Phe Trp Val Leu Val Val Val Gly Gly Val Leu Ala
370                 375                 380

Cys Tyr Ser Leu Leu Val Thr Val Ala Phe Ile Ile Phe Trp Val Arg
385                 390                 395                 400

Ser Lys Arg Ser Arg Leu Leu His Ser Asp Tyr Met Asn Met Thr Pro
                405                 410                 415

Arg Arg Pro Gly Pro Thr Arg Lys His Tyr Gln Pro Tyr Ala Pro Pro
                420                 425                 430

Arg Asp Phe Ala Ala Tyr Arg Ser Leu Arg Val Lys Phe Ser Arg Ser
                435                 440                 445

Ala Asp Ala Pro Ala Tyr Gln Gln Gly Gln Asn Gln Leu Tyr Asn Glu
450                 455                 460

Leu Asn Leu Gly Arg Arg Glu Glu Tyr Asp Val Leu Asp Lys Arg Arg
465                 470                 475                 480

Gly Arg Asp Pro Glu Met Gly Gly Lys Pro Gln Arg Arg Lys Asn Pro
                485                 490                 495

Gln Glu Gly Leu Tyr Asn Glu Leu Gln Lys Asp Lys Met Ala Glu Ala
                500                 505                 510

Tyr Ser Glu Ile Gly Met Lys Gly Glu Arg Arg Arg Gly Lys Gly His
                515                 520                 525

Asp Gly Leu Tyr Gln Gly Leu Ser Thr Ala Thr Lys Asp Thr Tyr Asp
                530                 535                 540

Ala Leu His Met Gln Ala Leu Pro Pro Arg Arg Ser Gln Cys Met Trp
545                 550                 555                 560

Pro Arg Glu Thr Gln Leu Leu Leu Glu Val Pro Pro Ser Thr Glu Asp
                565                 570                 575

Ala Arg Ser Cys Gln Phe Pro Glu Glu Glu Arg Gly Glu Arg Ser Ala
                580                 585                 590

Glu Glu Lys Gly Arg Leu Gly Asp Leu Trp Val
                595                 600

<210> SEQ ID NO 38
<211> LENGTH: 603
<212> TYPE: PRT
<213> ORGANISM: Artificial Sequence
<220> FEATURE:
<223> OTHER INFORMATION: Anti EGFR-z28G-CAR sequence

<400> SEQUENCE: 38

Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
                20                  25                  30

Pro Ser Glu Thr Leu Ser Leu Thr Cys Thr Val Ser Gly Gly Ser Ile
            35                  40                  45
```

```
Ser Ser Ser Ser Tyr Tyr Trp Gly Trp Ile Arg Gln Pro Pro Gly Lys
 50                  55                  60

Gly Leu Glu Trp Ile Gly Ser Ile Tyr Tyr Ser Gly Ser Thr Tyr Tyr
 65                  70                  75                  80

Asn Pro Ser Leu Lys Ser Arg Val Thr Ile Ser Val Asp Thr Ser Lys
                 85                  90                  95

Asn Gln Phe Ser Leu Lys Leu Ser Ser Val Thr Ala Ala Asp Thr Ala
                100                 105                 110

Val Tyr Tyr Cys Ala Arg Leu Pro Met Val Thr Met Ser Phe Asp Tyr
                115                 120                 125

Trp Gly Gln Gly Thr Leu Val Thr Val Ser Arg Gly Gly Gly Gly Ser
130                 135                 140

Gly Gly Gly Gly Ser Gly Gly Gly Ser Met Ala Ser Tyr Val Leu
145                 150                 155                 160

Thr Gln Pro Pro Ser Val Ser Val Ala Pro Gly Lys Thr Ala Arg Ile
                165                 170                 175

Thr Cys Gly Gly Asn Asn Ile Gly Ser Lys Ser Val His Trp Tyr Gln
                180                 185                 190

Gln Lys Pro Gly Gln Ala Pro Val Leu Val Ile Tyr Tyr Asp Ser Asp
                195                 200                 205

Arg Pro Ser Gly Ile Pro Glu Arg Phe Ser Gly Ser Asn Ser Gly Asn
210                 215                 220

Thr Ala Thr Leu Thr Ile Ser Arg Val Glu Ala Gly Asp Glu Ala Asp
225                 230                 235                 240

Tyr Tyr Cys Gln Val Trp Asp Ser Ser Asp His Val Val Phe Gly
                245                 250                 255

Gly Gly Thr Lys Leu Thr Val Leu Gly Gln Pro Lys Ala Ala Pro Ser
                260                 265                 270

Val Thr Leu Phe Pro Pro Ser Ser Glu Glu Leu Gln Ala Asn Lys Ala
                275                 280                 285

Thr Leu Val Cys Leu Ile Ser Asp Phe Tyr Pro Gly Ala Val Thr Val
                290                 295                 300

Ala Trp Lys Ala Asp Ser Ser Pro Val Lys Ala Gly Val Glu Thr Thr
305                 310                 315                 320

Thr Pro Ser Lys Gln Ser Asn Asn Lys Tyr Ala Ala Ser Ser Tyr Leu
                325                 330                 335

Ser Leu Thr Pro Glu Gln Trp Lys Ser His Arg Ser Tyr Ser Cys Gln
                340                 345                 350

Val Thr His Glu Gly Ser Thr Val Glu Lys Thr Val Ala Pro Thr Glu
                355                 360                 365

Cys Ser Thr Arg Phe Trp Val Leu Val Val Val Gly Gly Val Leu Ala
                370                 375                 380

Cys Tyr Ser Leu Leu Val Thr Val Ala Phe Ile Ile Phe Trp Val Arg
385                 390                 395                 400

Leu Arg Val Lys Phe Ser Arg Ser Ala Asp Ala Pro Ala Tyr Gln Gln
                405                 410                 415

Gly Gln Asn Gln Leu Tyr Asn Glu Leu Asn Leu Gly Arg Arg Glu Glu
                420                 425                 430

Tyr Asp Val Leu Asp Lys Arg Arg Gly Arg Asp Pro Glu Met Gly Gly
                435                 440                 445

Lys Pro Gln Arg Arg Lys Asn Pro Gln Glu Gly Leu Tyr Asn Glu Leu
450                 455                 460
```

```
Gln Lys Asp Lys Met Ala Glu Ala Tyr Ser Glu Ile Gly Met Lys Gly
465                 470                 475                 480

Glu Arg Arg Arg Gly Lys Gly His Asp Gly Leu Tyr Gln Gly Leu Ser
            485                 490                 495

Thr Ala Thr Lys Asp Thr Tyr Asp Ala Leu His Met Gln Ala Leu Pro
        500                 505                 510

Pro Arg Ser Lys Arg Ser Arg Leu Leu His Ser Asp Tyr Met Asn Met
    515                 520                 525

Thr Pro Arg Arg Pro Gly Pro Thr Arg Lys His Tyr Gln Pro Tyr Ala
530                 535                 540

Pro Pro Arg Asp Phe Ala Ala Tyr Arg Ser Arg Ser Gln Cys Met Trp
545                 550                 555                 560

Pro Arg Glu Thr Gln Leu Leu Leu Glu Val Pro Pro Ser Thr Glu Asp
            565                 570                 575

Ala Arg Ser Cys Gln Phe Pro Glu Glu Glu Arg Gly Glu Arg Ser Ala
        580                 585                 590

Glu Glu Lys Gly Arg Leu Gly Asp Leu Trp Val
    595                 600
```

<210> SEQ ID NO 39
<211> LENGTH: 603
<212> TYPE: PRT
<213> ORGANISM: Artificial Sequence
<220> FEATURE:
<223> OTHER INFORMATION: Anti EGFR-G28z-CAR sequence

<400> SEQUENCE: 39

```
Met Lys His Leu Trp Phe Phe Leu Leu Leu Val Ala Ala Pro Arg Trp
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Gly Ser Ile
        35                  40                  45

Ser Ser Ser Ser Tyr Tyr Trp Gly Trp Ile Arg Gln Pro Pro Gly Lys
    50                  55                  60

Gly Leu Glu Trp Ile Gly Ser Ile Tyr Tyr Ser Gly Ser Thr Tyr Tyr
65                  70                  75                  80

Asn Pro Ser Leu Lys Ser Arg Val Thr Ile Ser Val Asp Thr Ser Lys
                85                  90                  95

Asn Gln Phe Ser Leu Lys Leu Ser Ser Val Thr Ala Ala Asp Thr Ala
            100                 105                 110

Val Tyr Tyr Cys Ala Arg Leu Pro Met Val Thr Met Ser Phe Asp Tyr
        115                 120                 125

Trp Gly Gln Gly Thr Leu Val Thr Val Ser Arg Gly Gly Gly Gly Ser
130                 135                 140

Gly Gly Gly Gly Ser Gly Gly Gly Ser Met Ala Ser Tyr Val Leu
145                 150                 155                 160

Thr Gln Pro Pro Ser Val Ser Val Ala Pro Gly Lys Thr Ala Arg Ile
                165                 170                 175

Thr Cys Gly Gly Asn Asn Ile Gly Ser Lys Ser Val His Trp Tyr Gln
            180                 185                 190

Gln Lys Pro Gly Gln Ala Pro Val Leu Val Ile Tyr Tyr Asp Ser Asp
        195                 200                 205

Arg Pro Ser Gly Ile Pro Glu Arg Phe Ser Gly Ser Asn Ser Gly Asn
    210                 215                 220
```

-continued

| | | | | | | | | | | | | |
|---|---|---|---|---|---|---|---|---|---|---|---|---|
|Thr|Ala|Thr|Leu|Thr|Ile|Ser|Arg|Val|Glu|Ala|Gly|Asp|Glu|Ala|Asp|
|225| | | | |230| | | | |235| | | | |240|
|Tyr|Tyr|Cys|Gln|Val|Trp|Asp|Ser|Ser|Asp|His|Val|Val|Phe|Gly|
| | | | |245| | | | |250| | | | |255| |
|Gly|Gly|Thr|Lys|Leu|Thr|Val|Leu|Gly|Gln|Pro|Lys|Ala|Ala|Pro|Ser|
| | | |260| | | | |265| | | | |270| | |
|Val|Thr|Leu|Phe|Pro|Pro|Ser|Ser|Glu|Glu|Leu|Gln|Ala|Asn|Lys|Ala|
| | |275| | | | |280| | | | |285| | | |
|Thr|Leu|Val|Cys|Leu|Ile|Ser|Asp|Phe|Tyr|Pro|Gly|Ala|Val|Thr|Val|
| |290| | | | |295| | | | |300| | | | |
|Ala|Trp|Lys|Ala|Asp|Ser|Ser|Pro|Val|Lys|Ala|Gly|Val|Glu|Thr|Thr|
|305| | | | |310| | | | |315| | | | |320|
|Thr|Pro|Ser|Lys|Gln|Ser|Asn|Asn|Lys|Tyr|Ala|Ala|Ser|Ser|Tyr|Leu|
| | | |325| | | | |330| | | | |335| | |
|Ser|Leu|Thr|Pro|Glu|Gln|Trp|Lys|Ser|His|Arg|Ser|Tyr|Ser|Cys|Gln|
| | | |340| | | | |345| | | | |350| | |
|Val|Thr|His|Glu|Gly|Ser|Thr|Val|Glu|Lys|Thr|Val|Ala|Pro|Thr|Glu|
| | |355| | | | |360| | | | |365| | | |
|Cys|Ser|Thr|Arg|Phe|Trp|Val|Leu|Val|Val|Val|Gly|Gly|Val|Leu|Ala|
|370| | | | |375| | | | |380| | | | | |
|Cys|Tyr|Ser|Leu|Leu|Val|Thr|Val|Ala|Phe|Ile|Ile|Phe|Trp|Val|Arg|
|385| | | | |390| | | | |395| | | | |400|
|Arg|Ser|Gln|Cys|Met|Trp|Pro|Arg|Glu|Thr|Gln|Leu|Leu|Leu|Glu|Val|
| | | | |405| | | | |410| | | | |415| |
|Pro|Pro|Ser|Thr|Glu|Asp|Ala|Arg|Ser|Cys|Gln|Phe|Pro|Glu|Glu|Glu|
| | | |420| | | | |425| | | | |430| | |
|Arg|Gly|Glu|Arg|Ser|Ala|Glu|Glu|Lys|Gly|Arg|Leu|Gly|Asp|Leu|Trp|
| | |435| | | | |440| | | | |445| | | |
|Val|Ser|Lys|Arg|Ser|Arg|Leu|Leu|His|Ser|Asp|Tyr|Met|Asn|Met|Thr|
| |450| | | | |455| | | | |460| | | | |
|Pro|Arg|Arg|Pro|Gly|Pro|Thr|Arg|Lys|His|Tyr|Gln|Pro|Tyr|Ala|Pro|
|465| | | | |470| | | | |475| | | | |480|
|Pro|Arg|Asp|Phe|Ala|Ala|Tyr|Arg|Ser|Leu|Arg|Val|Lys|Phe|Ser|Arg|
| | | | |485| | | | |490| | | | |495| |
|Ser|Ala|Asp|Ala|Pro|Ala|Tyr|Gln|Gln|Gly|Gln|Asn|Gln|Leu|Tyr|Asn|
| | | |500| | | | |505| | | | |510| | |
|Glu|Leu|Asn|Leu|Gly|Arg|Arg|Glu|Glu|Tyr|Asp|Val|Leu|Asp|Lys|Arg|
| | |515| | | | |520| | | | |525| | | |
|Arg|Gly|Arg|Asp|Pro|Glu|Met|Gly|Gly|Lys|Pro|Gln|Arg|Arg|Lys|Asn|
| |530| | | | |535| | | | |540| | | | |
|Pro|Gln|Glu|Gly|Leu|Tyr|Asn|Glu|Leu|Gln|Lys|Asp|Lys|Met|Ala|Glu|
|545| | | | |550| | | | |555| | | | |560|
|Ala|Tyr|Ser|Glu|Ile|Gly|Met|Lys|Gly|Glu|Arg|Arg|Arg|Gly|Lys|Gly|
| | | | |565| | | | |570| | | | |575| |
|His|Asp|Gly|Leu|Tyr|Gln|Gly|Leu|Ser|Thr|Ala|Thr|Lys|Asp|Thr|Tyr|
| | | |580| | | | |585| | | | |590| | |
|Asp|Ala|Leu|His|Met|Gln|Ala|Leu|Pro|Pro|Arg|
| | | |595| | | | |600| | | |